United States Patent
Lo et al.

(10) Patent No.: US 9,545,210 B2
(45) Date of Patent: Jan. 17, 2017

(54) ACCURATELY INDETIFYING CRITCAL REGIONS IN ATRIAL FIBRILLATION BY IDENTIFYING ROTORS IN DIRECTIONAL SIMILARITY VECTOR FIELD

(71) Applicants: Yenn-jiang Lin, Taipei (TW); Men-Tzung Lo, Tainan (TW)

(72) Inventors: Men-Tzung Lo, Tainan (TW); Yenn-Jiang Lin, Taipei (TW); Huan-Yu Kuo, Jhongli (TW); Yi-Chung Chang, Jhongli (TW); Chen Lin, Jhongli (TW); Hsiang-Chih Chang, Jhongli (TW); Fa-Po Chung, Taipei (TW); Shih-Ann Chen, Taipei (TW)

(73) Assignees: Yenn-jiang Lin, Taipei (TW); Men-Tzung Lo, Tainan (TW)

( * ) Notice: Subject to any disclaimer, the term of this patent is extended or adjusted under 35 U.S.C. 154(b) by 0 days.

(21) Appl. No.: 14/699,171

(22) Filed: Apr. 29, 2015

(65) Prior Publication Data
US 2015/0230721 A1 Aug. 20, 2015

Related U.S. Application Data

(63) Continuation-in-part of application No. 14/474,302, filed on Sep. 2, 2014, which is a continuation-in-part of application No. 13/558,616, filed on Jul. 26, 2012, now Pat. No. 8,862,213.

(51) Int. Cl.
| | |
|---|---|
| *A61B 5/046* | (2006.01) |
| *A61B 5/04* | (2006.01) |
| *A61B 5/00* | (2006.01) |
| *A61B 5/0408* | (2006.01) |
| *A61B 18/14* | (2006.01) |
| *A61B 18/00* | (2006.01) |

(52) U.S. Cl.
CPC .......... *A61B 5/04011* (2013.01); *A61B 5/046* (2013.01); *A61B 5/04012* (2013.01); *A61B 5/04085* (2013.01); *A61B 5/4836* (2013.01); *A61B 5/7246* (2013.01); *A61B 18/1492* (2013.01); *A61B 2018/00351* (2013.01); *A61B 2018/00577* (2013.01); *A61B 2018/00839* (2013.01)

(58) Field of Classification Search
CPC ...................... A61B 5/046; A61B 2018/00839
USPC ......................... 600/509, 515, 518
See application file for complete search history.

(56) References Cited

U.S. PATENT DOCUMENTS 5,868,680 A 2/1999 Steiner

*Primary Examiner* — Allen Porter, Jr.
(74) *Attorney, Agent, or Firm* — SV Patent Service

(57) ABSTRACT

A computer-assisted method for quantitatively characterizing atrial fibrillation in a patient includes recording time series of bipolar atrial fibrillation signals at multiple sites in a patient's atria using two or more electrodes, calculating a similarity index vector by a computer system based on the bipolar atrial fibrillation signal between a first site and its neighboring sites, constructing an similarity-index vector field based on similarity-index vectors at different sites, calculating Curl and Divergence of the similarity-index vector field, calculating Rotor Identification using Curl and Divergence, calculating Focal Identification using Divergence, and determining one or more critical regions in the patient's atria if Rotor Identification is above a first predetermined threshold and Focal Identification is above a second predetermined threshold.

13 Claims, 25 Drawing Sheets

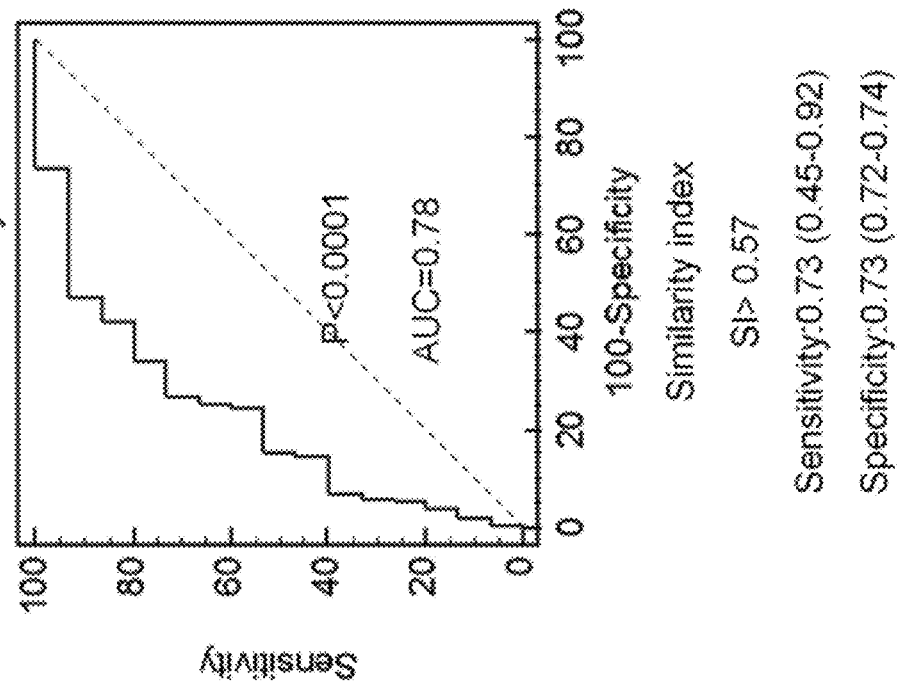
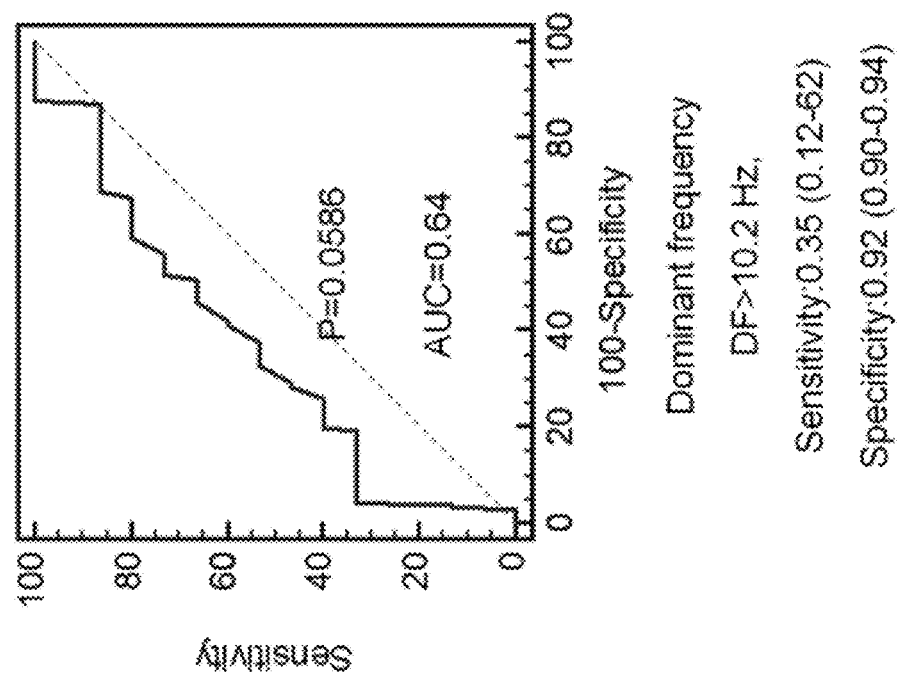
Figure 12A
Figure 12B

ACCURATELY INDETIFYING CRITCAL REGIONS IN ATRIAL FIBRILLATION BY IDENTIFYING ROTORS IN DIRECTIONAL SIMILARITY VECTOR FIELD

BACKGROUND OF THE INVENTION

The invention relates to the technologies for treating atrial fibrillation (AF), and in particular, to methods for determining nature of the atrial substrate and localizing critical regions in atrial fibrillation.

Atrial fibrillation is the most common type of tachyarrhythmia encountered in clinical practice. Catheter ablation is currently the standard therapy in patients who were refractory to antiarrhythmic medication. Pulmonary vein isolation (PVI) has become the mainstream catheter ablation technique for paroxysmal AF. For patients who have not responded to PVI, substrate modification with complex fractionated electrogram (CFE) ablation is considered to be necessary to treat persistent AF.

Conventional AF identification methods include dominant frequency (DF) analyses in frequency domain of consecutive electrograms, and CFE mean analysis in time domain of consecutive electrograms. Both methods produce average results based on activation intervals, which not applicable to diagnosing persistent or late stage AF patients. In particular, CFEs are usually observed in many regions of the atria, which make it difficult to identify critical atrial substrate using the conventional AF identification methods.

Recent clinical and animal studies have demonstrated that AF reentrant sources may be related to rotors, and the degree of electrogram similarity in the waveform propagating from the focal point can be an indicator for identifying the rotors.

For substrate mapping of AF, there is therefore a need to more accurate identification of critical regions and discriminate them from by-standers than conventional AF identification methods, especially, for accurate identification of rotor regions in persistent AF and facilitating electrophysiologist to search for the critical atrial substrate in maintaining AF.

SUMMARY OF THE INVENTION

The present application discloses an improved method for effectively identifying the substrate nature and localizing critical regions by more accurately analyzing atrial fibrillation signal from a patient. In contrast to conventional techniques that focus on the quantization of fractionality in the AF signals, the presently disclosed method is aimed to discover the repeating patterns among the fractionated AF signals to enhance the efficacy of catheter ablation and long-term outcome. For persistent AF, substrate modification with CFE ablation is considered to be necessary in patients who have not responded to PVI. However, CFEs are usually observed in many regions of the atria, making it difficult to identify critical atrial substrates. The presently disclosed method can discover regional disparities of the electrogram characteristics between the important CFE and the bystander CFEs which are difficult to identify by the interval analysis, dominant frequency value, and the temporal variation of the DF peaks (bandwidth of the DF peaks or the harmonic index in Fourier spectrum of AF signal). The presently disclosed method can differentiate those sites with repeating patterns from the bystander CFE and thus increase the rate of successful procedural AF terminations and long-term outcome after the first ablation procedure.

As described above, a rotor can be one of the significant mechanisms for AF maintenance in patients with persistent AF after PVI. Moreover, the repeating patterns could occur in the vicinity of the rotor. The presently disclosed method has developed Similarity Index vectors (SI vectors) to investigate the electrogram data of cardiac fibrillation. The disclosed method calculates bipolar repetitiveness from a continuous recording of ECG signal. An SI vector field is obtained, which demonstrates the behavior of wavefront propagation over time. The SI vector field is quantitatively characterized by mathematical operators Curl and Divergence. Rotor Identification (RI), defined as the product of Curl and Divergence, describes wavefront rotating around and spreading outward from a rotor center. Focal Identification (FoI), defined the square of Divergence, characterizes wave propagation spreading around and out from a focal point. Using RI and FoI, the disclosed method can effectively identify small-radius reentry rotors in highly fractionated electrograms recorded from patients with persistent AF.

In a general aspect, the present invention relates to a computer-assisted method for quantitatively characterizing atrial fibrillation in a patient, including recording time series of bipolar atrial fibrillation (AF) signals at multiple sites in a patient's atria using two or more electrodes; calculating a similarity index (SI) vector by a computer system based on the bipolar AF signal between a first site and its neighboring sites, which includes the steps of: segmenting the time series of the AF signal into activation segments; obtaining local activation waveforms (LAW) from the activation segments; calculating SI based on similarity between the LAWs obtained from the activation segments; and determining a propagating direction of the bipolar AF signal. The computer-assisted method also includes constructing an SI vector field based on SI vectors at different sites; calculating Curl and Divergence of the SI vector field; calculating Rotor Identification (RI) using Curl and Divergence; calculating Focal Identification (FoI) using Divergence; and determining one or more critical regions in the patient's atria if RI is above a first predetermined threshold and FoI is above a second predetermined threshold.

Implementations of the system may include one or more of the following. The one or more critical regions in the patient's atria can be modified with complex fractionated electrogram (CFE) ablation. The bipolar AF signals can be recorded in time series at multiple sites in a patient's atria, wherein the SI vector field demonstrates wave propagations in the time series. The computer-assisted method can further include determining a size and a shape of an integral path for calculating Curl and Divergence of the SI vector field. The integral path can be along or within the patient's heart. RI is product of Curl and Divergence of the SI vector field. RI can characterize a rotor in the patient's atria, wherein the step of determining is at least in part based on an identification of a rotor in the patient's atria. FoI can be square of Divergence of the SI vector field. FoI can characterize a focal point in the patient's atria, wherein the step of determining is at least in part based on an identification of a focal point in the patient's atria. The step of calculating SI can include calculating a first similarity index based on similarity between the LAWs obtained from positive portions of the AF signal in the activation segments; calculating a second similarity index based on similarity between the LAWs obtained from negative portions of the AF signal in the activation segments; and determining a propagating direction of the bipolar AF signal based on magnitudes of the first similarity index by the second similarity index. The propagating direction of the bipolar AF signal can be from the first site to one of its neighboring sites if the first similarity index is larger than the second similarity index between the first site and the one of its neighboring sites. The propagating direction of the bipolar AF signal can be from one of its neighboring sites to the first site if the first similarity index is larger than the second similarity index between the first site and the one of its neighboring sites. The SI vector can be determined by the propagating direction and the larger one of the first similarity index by the second similarity index. The activation segments in the step of calculating a SI vector can be sequential in the time series of the AF signal. The step of calculating SI based on similarity between the LAWs obtained from the activation segments can further include representing each one of the LAWs by a vector based on strengths of the AF signal at a plurality of sampling points in a respective one of the LAWs; and computing a distance between vectors of a pair of LAWs obtained from the same time series of the AF signal to determine degrees of similarity between the pair of LAWs. The distances can be calculated between successive LAWs or between non-adjacent LAWs. The activation segments can be identified at least in part based on overlapping of local maxima in the time series of the AF signal. The step of calculating SI based on similarity between the LAWs obtained from the activation segments can further include normalizing the LAWs in the activation segments before the step of determining degrees of similarity between LAWs.

Although the invention has been particularly shown and described with reference to multiple embodiments, it will be understood by persons skilled in the relevant art that various changes in form and details can be made therein without departing from the spirit and scope of the invention.

BRIEF DESCRIPTION OF THE DRAWINGS

The following drawings, which are incorporated in and form a part of the specification, illustrate embodiments of the present invention and, together with the description, serve to explain the principles of the invention.

FIG. 12A is a plot of a receiver operating characteristic (ROC) curve showing an optimal threshold in detecting the termination sites within the continuous CFEs obtained by a conventional algorithm based on dominant frequency value.

FIG. 12B is a plot of a ROC curve showing optimal threshold in detecting the termination sites within the continuous CFEs obtained by an algorithm based on similarity index.

FIG. 16A shows a series of activations recorded by optical mapping. FIG. 16B shows maps of SI vector field, a divergence field calculated by integration of a closed loop with radius R=10, a divergence field and a curl field both calculated by integration of a close loop with radius R=4. The magnitude of field on each site represents in color from −1 to 1. FIG. 16C shows the maps of Rotor Identification (RI), Focal Identification (FoI), and Phase singularity (PS).

DETAILED DESCRIPTION OF THE INVENTION

Figure 1:
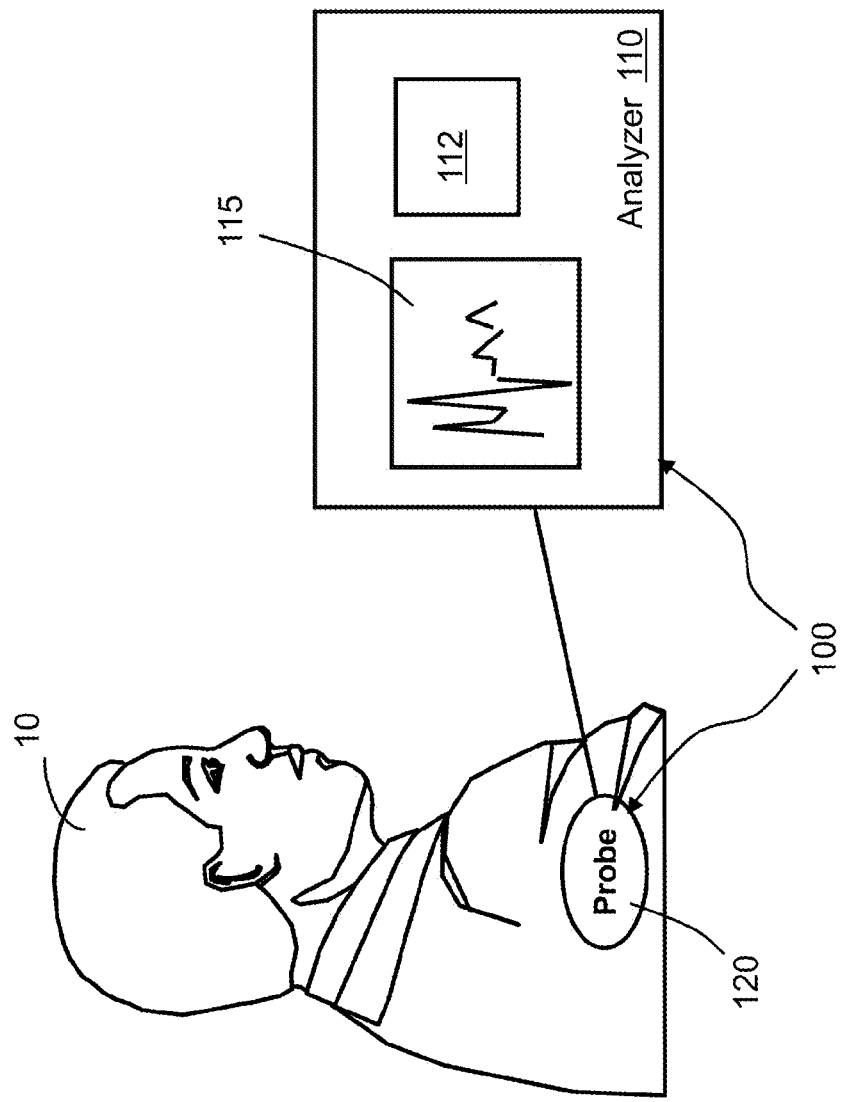
FIG. 1 is a schematic diagram of a system for evaluating atrial fibrillation in accordance to the present invention.

Referring to FIG. 1, an AF evaluation system 100 includes an analyzer 110 and a probe 120 that can be attached to a patient 10. The probe 120 can include a sensor, a transducer, or an electrode configured to measure intracardiac AF signals from the patient 10. The probe 120 can send the AF signals to the analyzer 110, often in analog form. The analyzer 110 can include an analog-to-digital (A/D) converter for digitizing the AF signals. The analyzer 110 also includes a computer processor 112 that is configured to process and analyze the AF signals after the AF signals are digitized by the A/D converter. A pre-stored algorithm in the analyzer 110 can rapidly analyze the AF signals, and provide guidance to defibrillation treatments, as described in more detail below. The analyzer 110 can also include necessary input/output devices, and a display 115 for displaying the AF signals and the results of the analysis of the AF signals.

Figure 2:
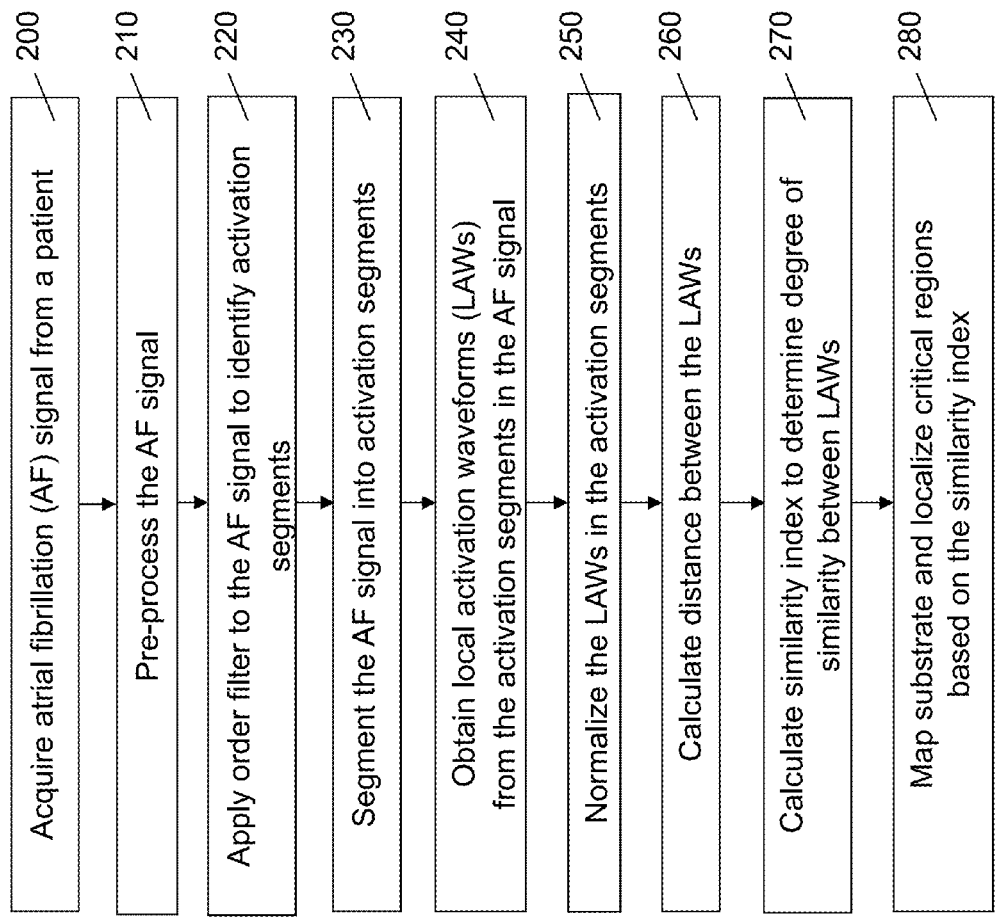
FIG. 2 is a flow diagram for processing and analyzing an atrial fibrillation signal to identify substrate nature and localize critical regions in patient's atria in accordance to some embodiments of the present invention.
Figure 3A:
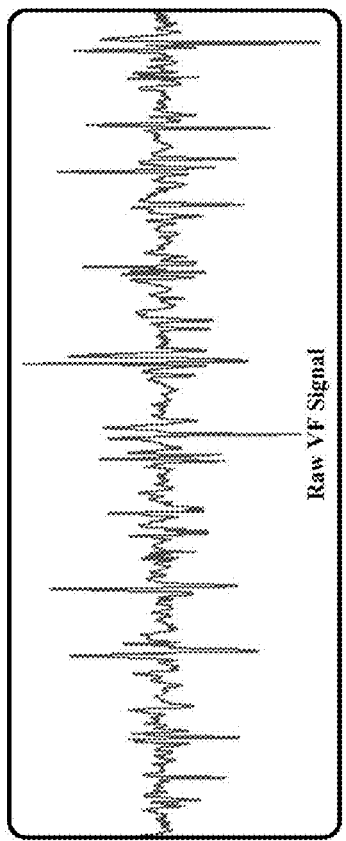
FIG. 3A illustrates a raw AF signal obtained by the system in FIG. 1.

In some embodiments, referring to FIG. 2, a process for analyzing a AF signal to identify substrate nature and localize critical regions include one or more of the following steps: a time series of a AF signal, shown in FIG. 3A, is recorded from a patient suffering from atrial fibrillation as described in relation to FIG. 1 above (step 200).

Figure 3B:
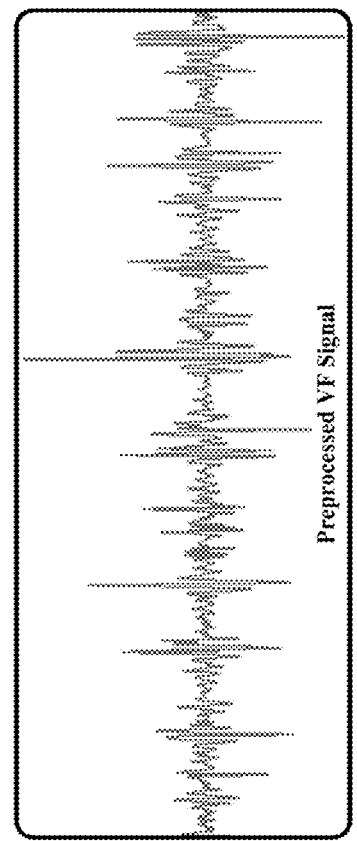
FIG. 3B illustrates pre-processing of the AF signal.

Optionally, the time series of AF signal is preprocessed (step 210). For example, as shown in FIG. 3B, the AF signal can be processed by band filtering to filter out high and low frequency noises.

Figure 4A:
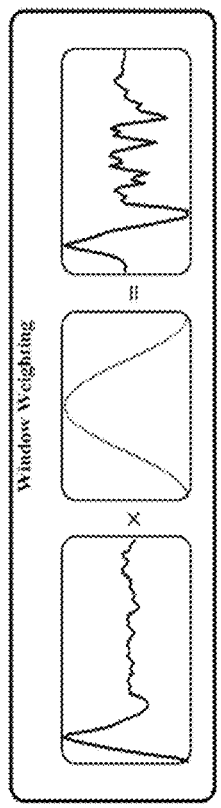
FIGS. 4A-4E illustrate segmentation of the AF signal after pre-processing.
Figure 4B:
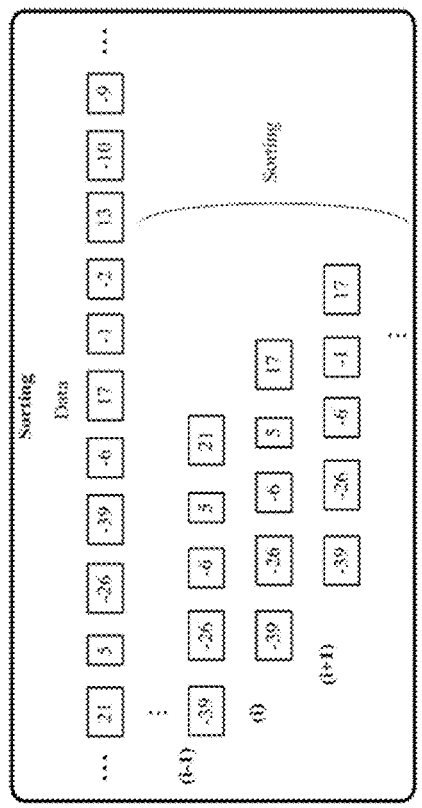
Figure 4C:
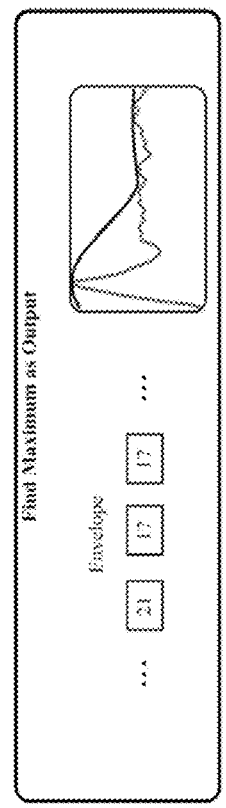

Next, referring to FIGS. 2 and 4A-4E, an order filter is then applied to the time series of AF signal (optionally filtered as described above) to identify activation segments (step 220). The time series of AF signal (the left curve in FIG. 4A) is weighted by a sliding window (the middle curve in FIG. 4A). The largest number among the weighted data (the right curve in FIG. 4A) within each sliding window is obtained as output. The window is shifted forward by 1-point each time and the procedure was repeated for each windowed data until the entire time series of AF signal is analyzed (FIG. 4B). After the envelope is obtained, the local activity peak is determined by finding the points with equal magnitude on the AF signal and envelope (FIG. 4C).

Figure 4D:
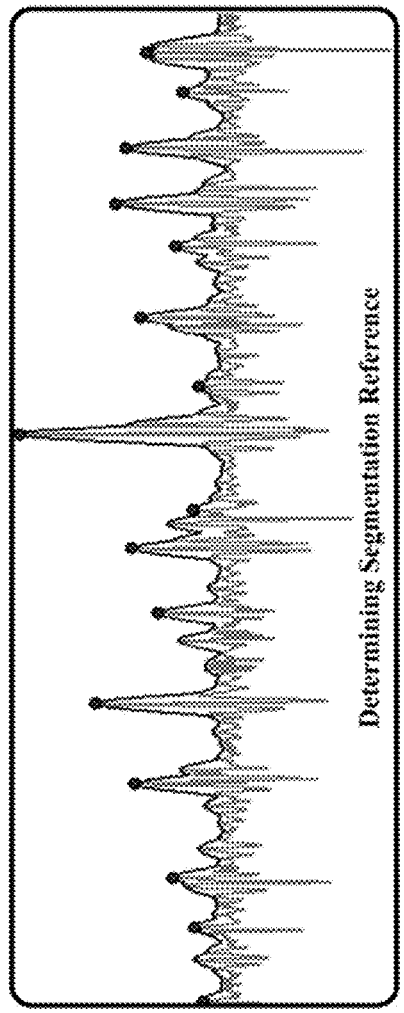
Figure 4E:
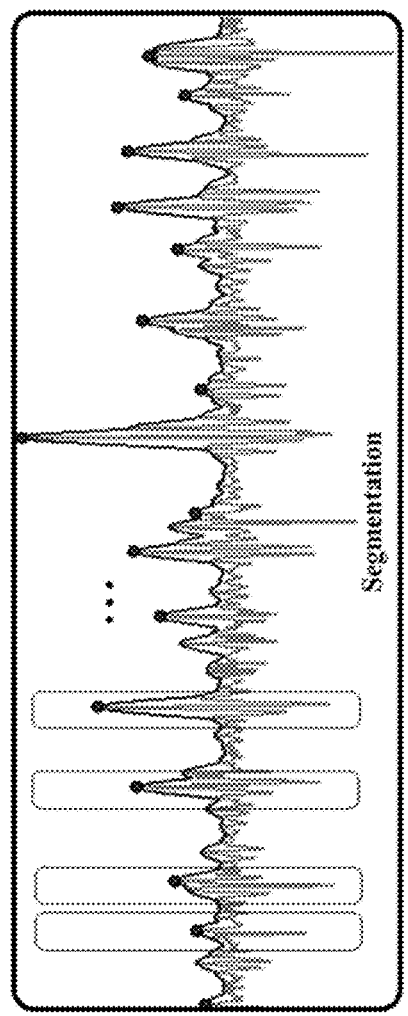

FIG. 4D shows the local activity peaks of the time series of AF signal. The time series of AF signal is segmented into activation segments based on the local activity peaks (FIG. 4E) (step 230). Details about the segmentation of the AF signal are described below in relation to FIG. 8. In some embodiments, the segmented windows in FIG. 4E can have the same width for the different activation segments. For example, the window width can be set as 55 msec.

Figure 5A:
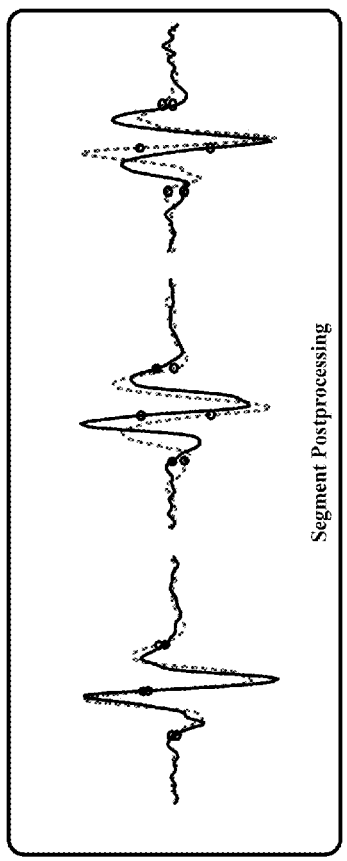
FIG. 5A illustrates local activation waveforms (LAWs) extracted from different segments and the post-processing of the LAWs.

Each segment includes a local activity waveform (LAW). A plurality of LAWs are cut out from the time series of AF signal as shown in FIG. 5A (step 240). The elements of each LAW $x_i$ (composed by m samples) can be regarded as a component of each dimension in an m-dimensional real space, and $x_i$ represented one point in this m-dimensional space.

Figure 5B:
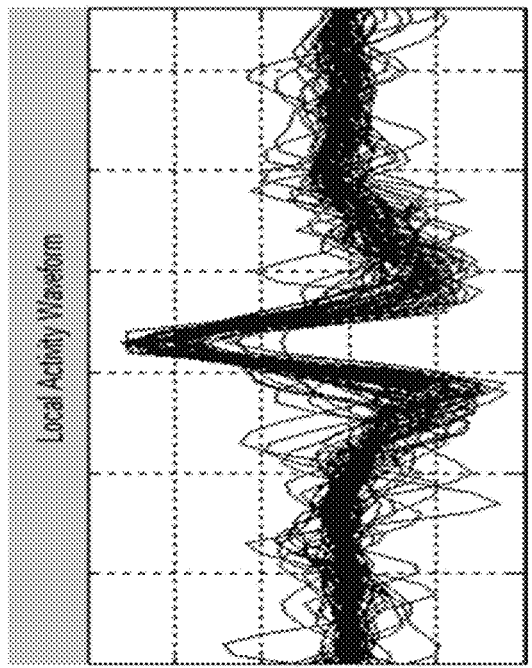
FIG. 5B shows normalized LAWs from different segments.

The segmented AF signal, as shown in FIG. 5A, is normalized (i.e. post-processing) (step 250). The normalized LAWs are shown in FIG. 5B. Each LAW was normalized to eliminate the variation of the amplitude of LAWs. Specifically, the normalization is achieved by dividing the LAW $x_i$ by its standard norm as denoted by $$s_i = \frac{x_i}{\sqrt{\sum_{j=1}^{m} x_{ij}^2}} \tag{1}$$

where $s_i$ is the $i^{th}$ normalized LAW. Similar to the case of $x_i$ representing a point of the m-dimensional real space, the $i^{th}$ normalized LAW $s_i$ represents a point in the m-dimensional unitary sphere.

The distances between every pairs of LAWs (including adjacent and non-adjacent LAWs) were then defined by the standard metric of the sphere as given by $$d(s_i, s_j) = \cos^{-1}(s_i \cdot s_j) \tag{2}$$

where $s_i$ and $s_j$ represent the $i^{th}$ and $j^{th}$ normalized LAW and (·) denotes the scalar product. The distances between LAWs shown in FIG. 5B are calculated (step 260).

Figure 6A:
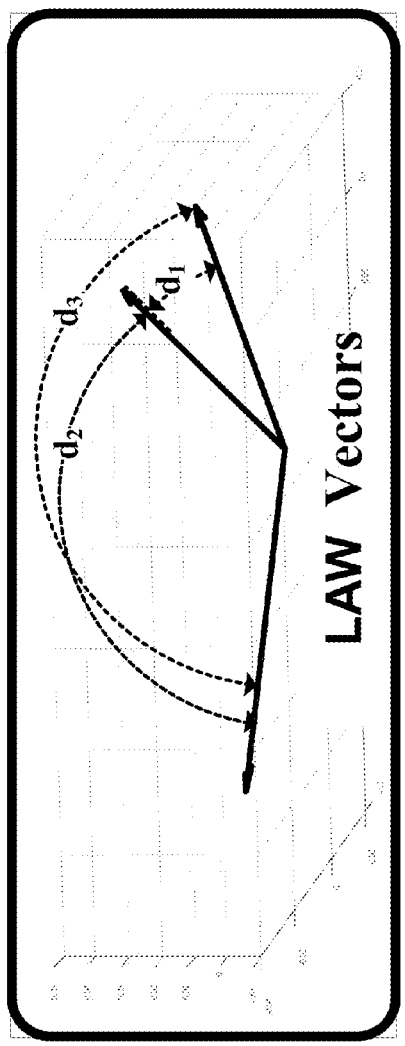
FIG. 6A shows angles between different pairs of LAW vectors.

LAW vectors are constructed as illustrated in FIG. 6A. A similarity index (ρ) is then calculated based on the angles between LAW vectors (i.e. the distance between the associated LAWs). The similarity index (ρ) is inversely proportional to angle between LAW vectors (and to the distance between the associated LAWs). If the angle between LAW vectors of a pair of LAWs is smaller than a pre-determined threshold, this LAW pair is regarded as similar, and vice versa.

The similarity index ρ(ε) is defined as the ratio of the number of similar LAW pairs to the total number of LAW pairs in the analyzed recording $$\rho(\varepsilon) = \frac{2}{N(N-1)} \sum_{i=1}^{N} \sum_{j=i+1}^{N} \Theta(\varepsilon - d(s_i \cdot s_j)) \quad \Theta(x) = \begin{cases} 1, \forall x > 0 \\ 0, \forall x \leq 0 \end{cases} \tag{3}$$

Figure 6B:
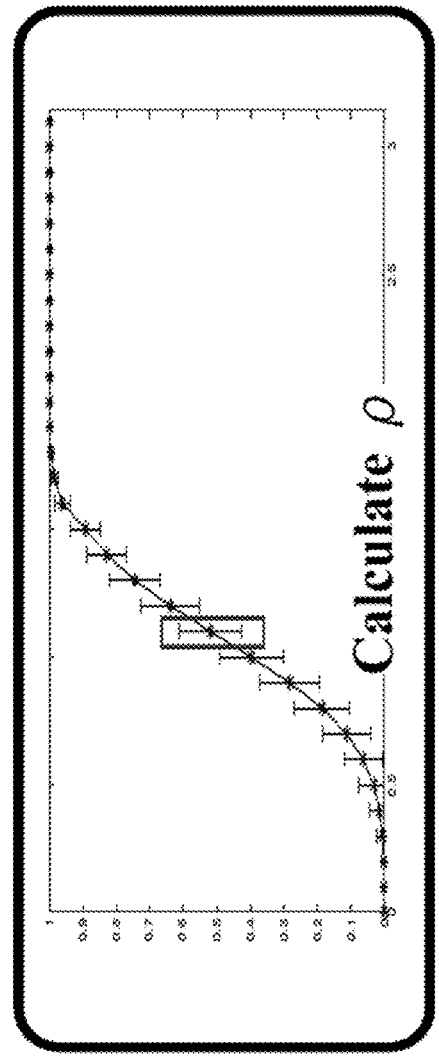
FIG. 6B shows cumulative distribution of similarity index (ρ) based on the angles between the LAW vectors and an optimal threshold in the cumulative distribution of the similarity index for determining termination sites within the continuous CFEs.

In Equation (3), the parameter ε is an adjustable threshold. By comparing the distance between two LAWs derived in Equation (2) to the threshold distance ε, we determined these two LAWs to be similar if the distance d was less than ε, or dissimilar if d was greater than or equal to ε. A concept illustration of the 3D case (i.e., m=3, where m is the window length of LAWs) is given in FIG. 6B. A cumulative distribution of similarity index (ρ) is calculated. An optimal threshold ε can be determined in the cumulative distribution of similarity index (ρ) to determine degree of similarity between LAWs as (step 270). LAWs higher than the threshold in the cumulative distribution of ρ are considered as resembling each other.

For a given ε, the similarity index ρ(ε) in Equation (3) can be used to indicate the probability of finding similar LAW pairs in the analyzed AF electrogram. Although the values of the pre-defined parameters (e.g. ε and m) may alter the results of ρ, the values of ρ were similar within certain ranges of pre-defined parameters by using peak alignment and for the best discriminative performance. In one non-limiting example, the window length of LAWs and ε are set to 50 msec and 1.1 respectively.

The critical regions are then mapped in the substrate based on the similarity index or the resemblance of LAWs, as shown in FIGS. 7A-7D, which identifies critical regions (step 280). In the present application, the term substrate means the cardiomyocytes located in the region-of-interested of atria. Modification often means the ablation procedure perform on the substrate.

Figure 7A:
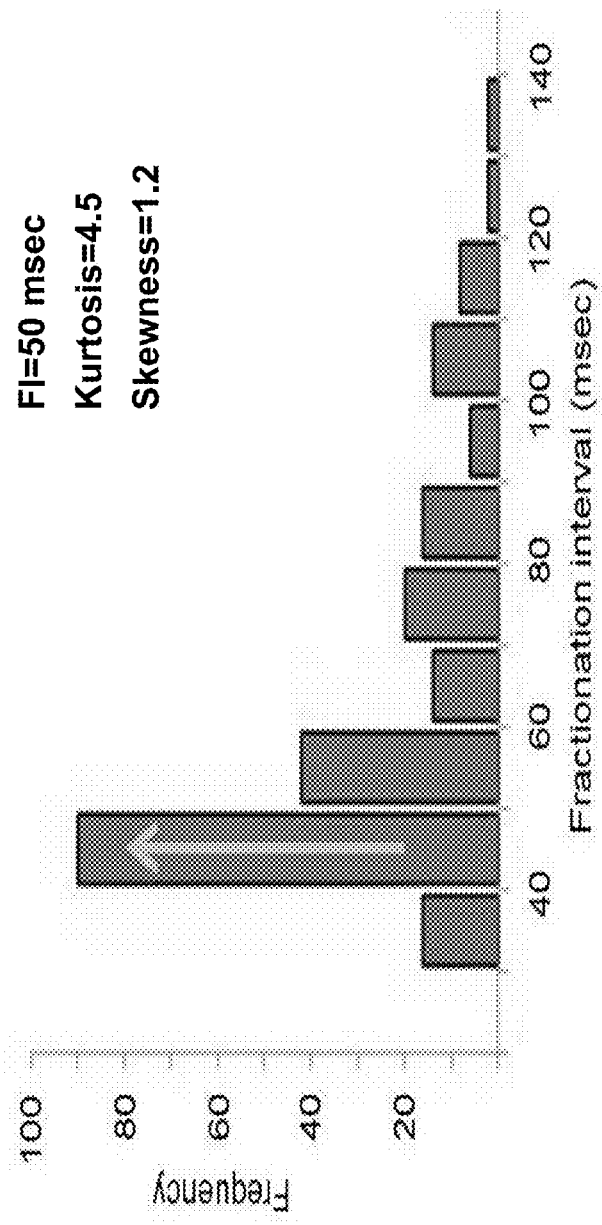
FIGS. 7A and 7B show histogram analysis of fractionation interval over 6 seconds at an AF termination site.
Figure 7B:
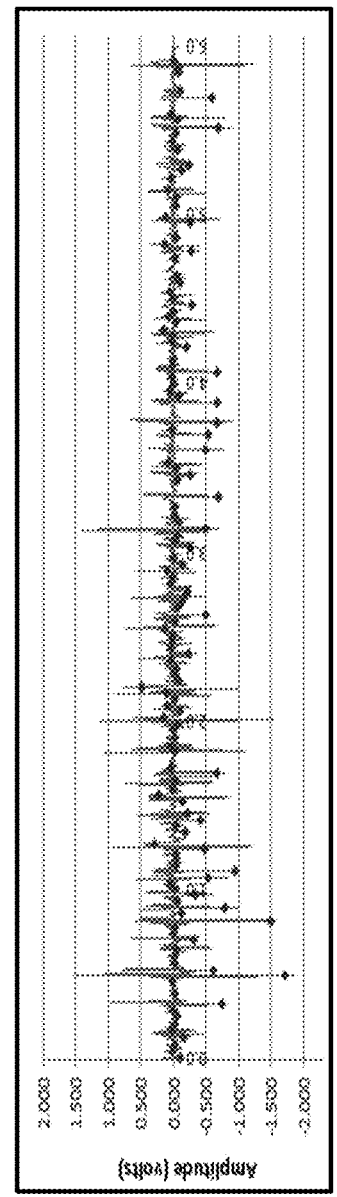
Figure 7C:
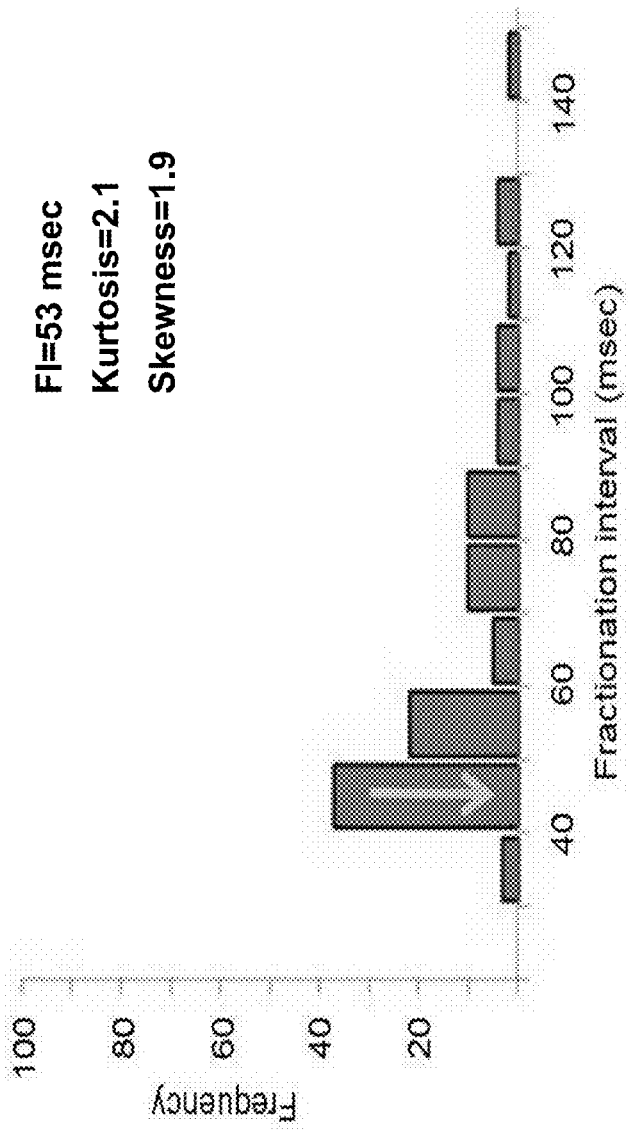
FIGS. 7C and 7D show histogram analysis of fractionation interval over 6 seconds at a continuous CFE site.
Figure 7D:
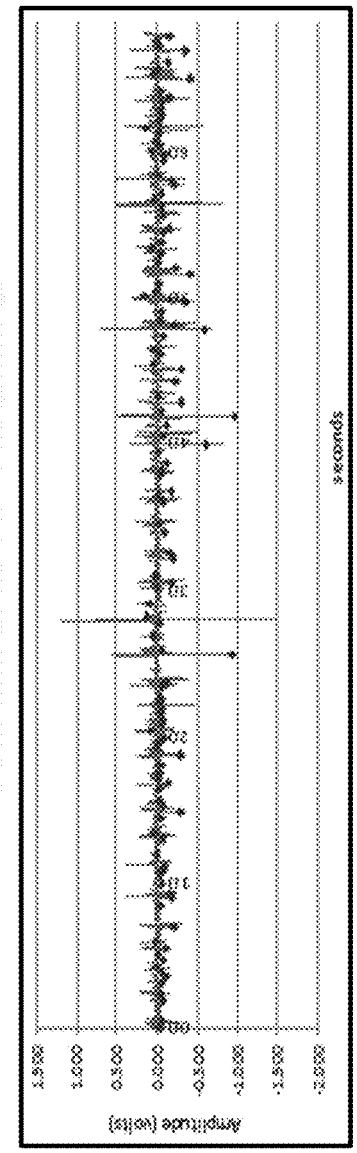

FIGS. 7B and 7D demonstrate the AF electrograms recorded from two different sites and the corresponding distribution of deflection intervals.

FIGS. 7A and 7B respectively show histogram and fractionation interval over 6 seconds at an AF termination site. The histogram (FIG. 7A) at this site exhibits a high kurtosis (of 4.5) with a sharp peaked distribution and positive skewness. This site exhibited a continuous fractionated signal of 50 msec.

FIGS. 7C and 7D show histogram analysis and fractionation interval over 6 seconds at a continuous CFE site. The histogram (FIG. 7C) at this site exhibits a low kurtosis (of 2.1) and positive skewness, whereas this site exhibits a continuous fractionated signal of 53 msec. CFE-targeted ablation at this site did not terminate AF.

Although mean values of the distribution of interval deflections for the two sites described above are similar (50 msec vs. 53 msec), but their Kurtosis values are quite different (4.5 vs. 2.1). It is discovered in the present invention that that the ablation on the site with high kurtosis can terminate the AF.

As described above, for longer duration AF, substrate modification with a complex fractionated electrogram ablation is considered to be necessary in patients who do not respond to PVI. The development of automated analysis algorithms for electrogram fractionation is important for a reproducible and objective assessment of this technique. However, most of the algorithms have been based on the mean fractionation interval (FI) between the deflection of the time-domain electrograms, such as the CFE-mean of the NavX system or shortest complex interval of the CARTO system. Detection is based on 3 criteria, set by the user, in which the deflection must: (1) exceed an adaptive peak-to-peak sensitivity threshold that is set at a reference-amplitude slightly greater than the baseline noise; (2) possess a down-stroke morphology for which the leading maximum and trailing minimum amplitudes occur within a time duration that is set to minimize the detection of broad, far-field events; and (3) exceed a refractory period after the previous detection that is set to minimize multiple detections on a single deflection event. The variation in the FIs acquiring by those modalities may be important for the interpretation of the substrate characteristics. Therefore, if the local FIs are not normally distributed, there is a limitation of the mean FI with a clinical application due to the temporal variation.

The present application discloses that the temporal variation in the annotated FI can provide important information to determine the features of critical CFEs in addition to the conventional FI algorithm. i.e., the local consistency of the fractionated electrograms can be assessed according to the distribution of FIs for a recording duration. The assessed electrograms in each patient were acquired and characterized by the "kurtosis" of the FI distribution. Briefly summarized, kurtosis measures the shape of distribution of the fractionated intervals within the window beyond simply using their mean or standard deviation. The value of kurtosis gives the relationship between each of the FIs to their mean. The higher the value of kurtosis, the less probable that FIs deviate from their mean.

Figure 8:
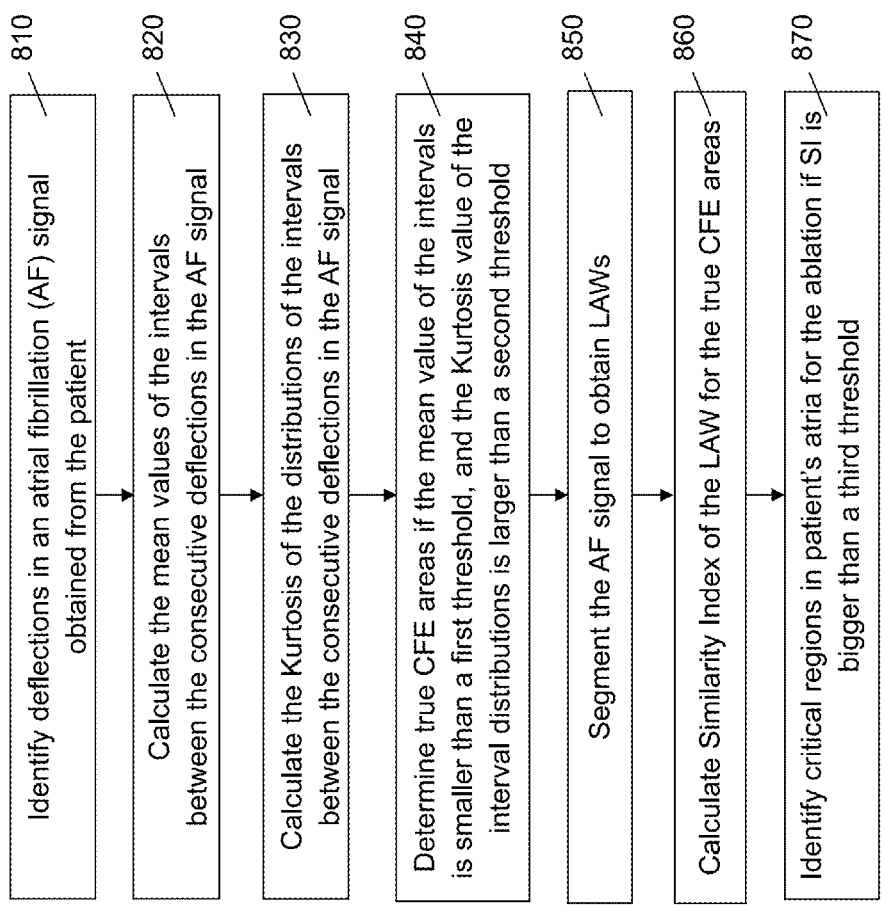
FIG. 8 is a flow diagram showing detailed steps of segmenting an atrial fibrillation signal to identify critical regions in patient's atria in accordance to some embodiments of the present invention.

In some embodiments, referring to FIG. 8, the presently disclosed method identifies critical regions (i.e. the "crucial" or "true" CFE) and discriminates them from by-standers by one or more of the following detailed steps: deflections in an AF signal are identified (step 810). The intervals between the consecutive deflections are calculated. The mean value of the intervals is calculated (step 820). The Kurtosis of the interval distributions is calculated (step 830). True CFE areas for the ablation are determined based on the criteria: mean value of the intervals is smaller than a first threshold, and the Kurtosis value of the interval distributions is larger than a second threshold (step 840).

In some embodiments, the operation accuracy can be further improved by segmentation steps as described in FIG. 2. The time series of the AF signal can be segmented into activation segments to obtain LAWs, as described above (step 850). Similarity index between LAWs is calculated for the areas identified (step 860). The critical regions in the patient's atria for the ablation are identified if SI is bigger than a third threshold (step 870).

If the areas which are identified as the true CFE are still extensive, the present disclosed method further identifies critical regions and discriminate them from by-standers, the presently disclosed method evaluates characteristics of a region by more accurately analyzing AF signal including: an elaborative segmentation to the AF signal and quantitative assessment of the repeating patterns in AF signal.

Mechanistic Considerations

The above described process is based on the following mechanistic considerations: Previous studies demonstrated the efficacy of adjunctive CFE ablation in addition to circumferential PVI. Considering that CFEs may play an active role in persistent AF, a CFE that maintains AF should be continuous and stable over time. Based on the time-domain signal, catheter ablation at sites displaying a greater percentage of continuous activity was associated with slowing or procedural AF termination (successful stop of AF) by catheter ablation in chronic AF. In recent years, automatic algorithms for 3D mapping systems have provided a rigorous quantitative analysis enabling the identification of the continuous CFEs and stability of the CFE distribution over time.

Mathematically, the morphological change over the distribution of the deflection types, total duration of the discrete electrograms, and intervals between consecutive deflections within the segmented windows, all contributed to the measurement of the stationarity feature of the electrograms. To non-paroxysmal AF patients, it is important to differentiate the culprit CFEs from the bystander CFEs. The stability of the electrograms may also reflect the presence of a focal pattern of activation.

Assuming consistent wavefront dynamic and activation patterns are emanating from the AF sources, repetitive waveforms of similar electrogram morphology should appear near the potential AF maintainers. A higher level of the electrogram similarity index over time at the continuous CFEs was more likely to respond to substrate modification. This can provides an alternative mapping tool to guide substrate modification.

Validation

One hundred consecutive persistent AF patients that received catheter ablation have been studied using the method described above. A total of 9558 fibrillatory electrograms were analyzed in this study (139±30 sites per patient in left atrium (LA).

Substrate Mapping of the Global Atria

Figure 9A:
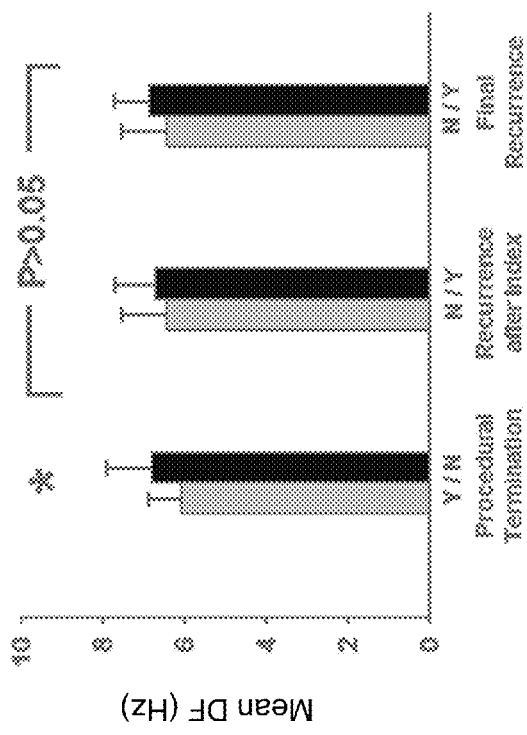
FIG. 9A shows the use of mean dominant frequency of the left atrium for predicting AF procedural termination, recurrence after the first ablation procedure, and recurrence after the final procedure.

FIG. 9A shows mean dominant frequency (DF) of the left atrium for predicting AF procedural termination, recurrence after the first ablation procedure, and recurrence after the final procedure. The phrase "procedure termination" means successfully stop the AF by catheter ablation. The phrase "recurrence after index" means the AF occurs again in some specific duration (e.g., in a month or half year). The phrase "final recurrence" means although AF disappears during the duration above, it occurs finally.

Figure 9B:
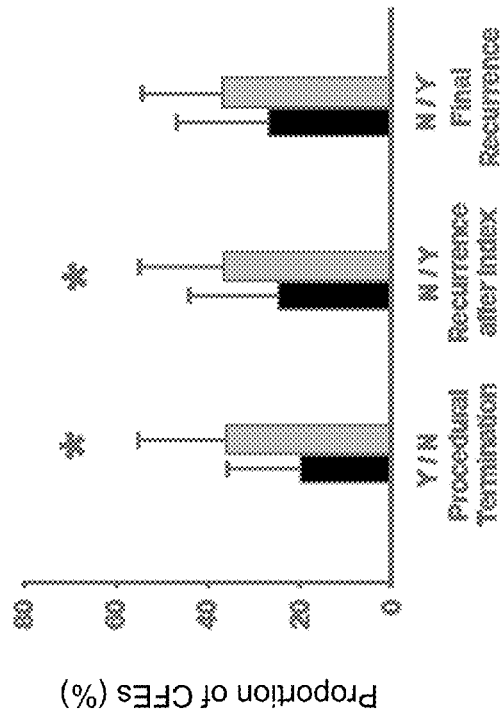
FIG. 9B shows the use of proportion of the continuous CFEs of the left atrium for predicting AF procedural termination, recurrence after the first ablation procedure, and recurrence after the final procedure.

FIG. 9B shows proportion of the continuous CFEs of the left atrium for predicting AF procedural termination, recurrence after the first ablation procedure, and recurrence after the final procedure. In FIGS. 8A and 8B, the * symbol means the discriminant performance is successful and reliable. "Y" and "N" respectively mean "True" and "False".

FIGS. 9A and 9B show comparisons of electrogram characteristics of the entire left atrium in the patients who did and did not respond to CFE ablation in terms of procedural AF termination and long-term AF recurrence (efficacy of single and multiple procedures without drugs). Patients with atrial substrate characteristics harboring rapid activity and more fractionated electrograms are less likely to respond to CFE ablation, as indicated by a higher DF (dominant frequency) (P>0.05), and higher proportion of CFEs in the left atrium (P<0.01), wherein the p-value is defined as the probability of obtaining a test statistic at least as extreme as the one that was actually observed.

To identify possible target of ablation, previous studies used the dominant frequency (DF) and the location with highest DF as the target. However, FIG. 9A shows result using the "first generation method" (conventional method) in which DF value has a P-value larger than 0.05 for all the recurrence patients and is no longer effective for discrimination.

FIG. 9B illustrates that the presently disclosed method based on proportion of continuous CFE is a better index for discriminating/predicting the results: whether the P-value is larger than 0.05 or not is critical. FIG. 9B also shows that continuous CFE (the "second generation method") is somehow effective since the proportion of continuous CFE become higher on persistent patients, but we obviously cannot ablate all the substrate with continuous CFE. So there is still a need for better identifying ablating targets.

Correlation of Ablation Outcome and Electrogram Characteristics

Figure 10A:
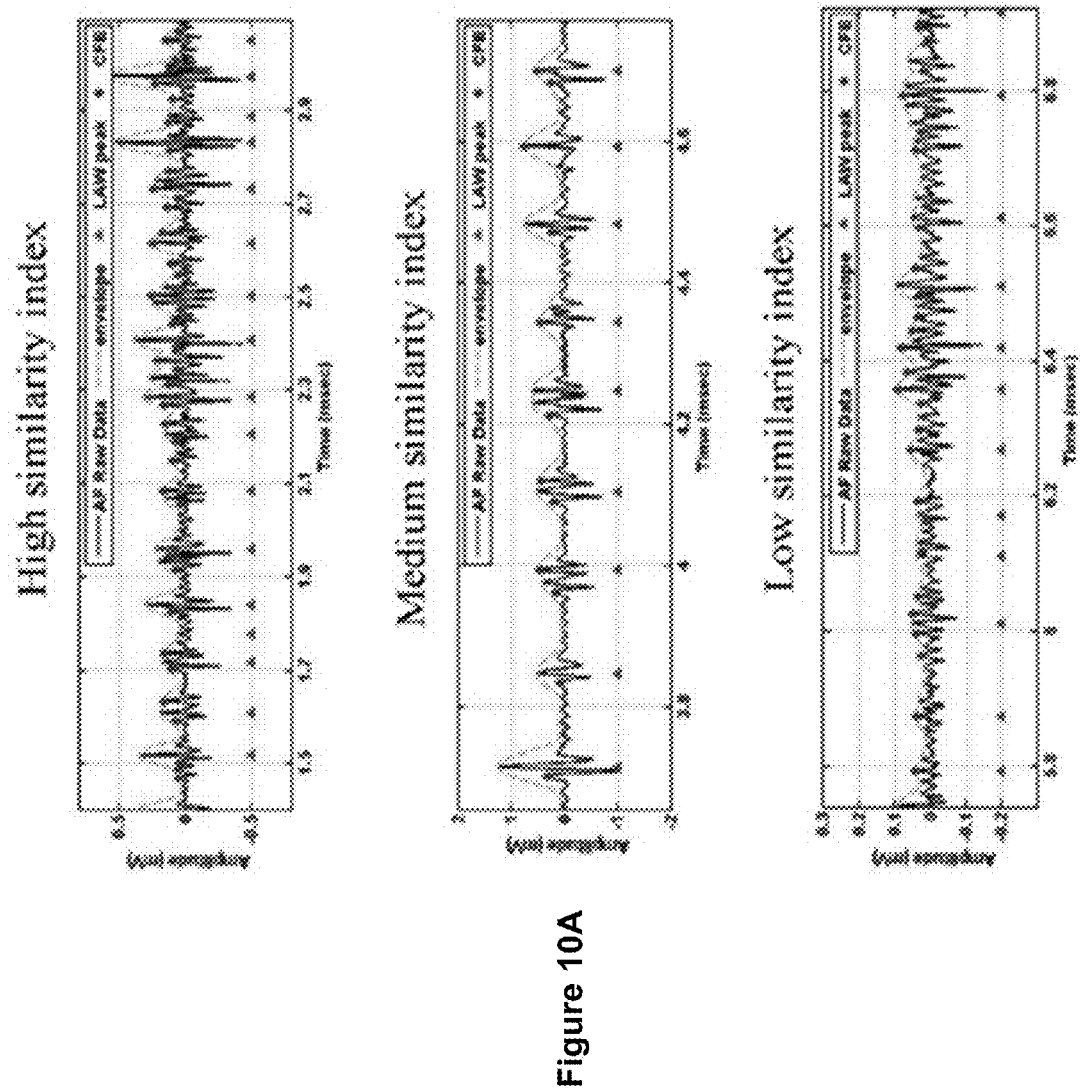
FIG. 10A show exemplified continuous complex fractionated electrograms having high, medium, and low similarity indices.
Figure 10B:
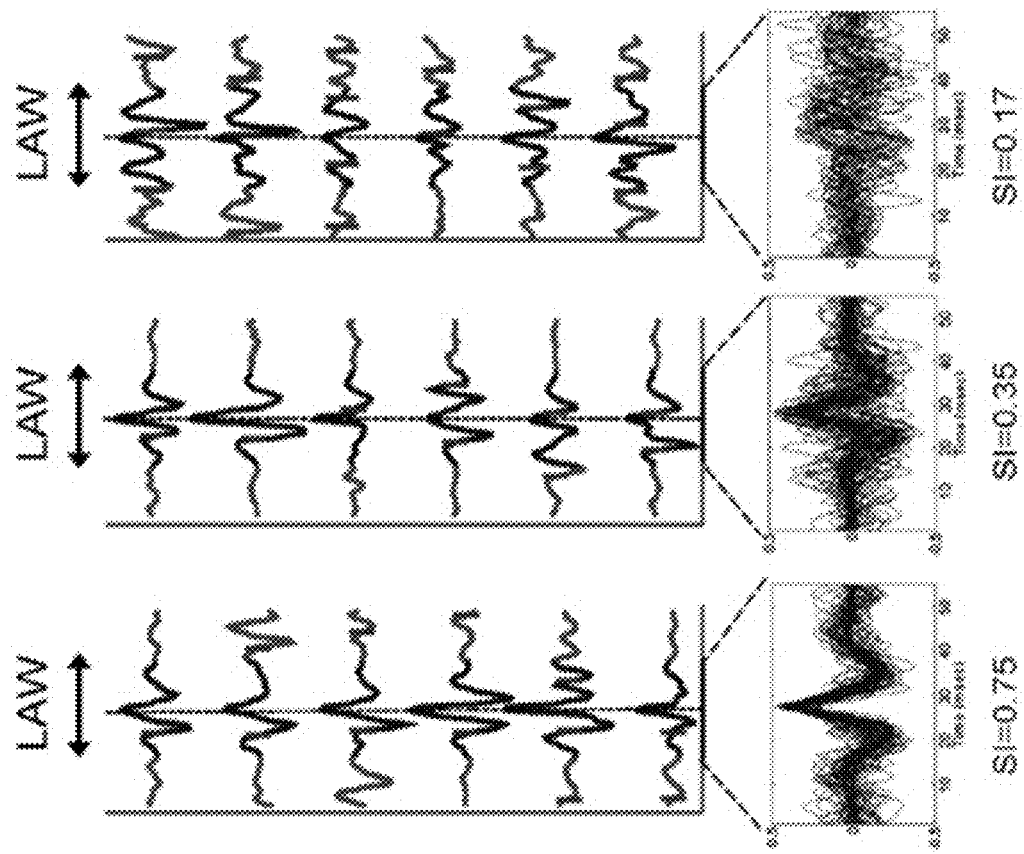
FIG. 10B shows LAWs respectively obtained from the complex fractionated electrograms having different similarity indices in FIG. 10A.

FIGS. 10A and 10B show analysis of the electrogram similarity with different types of continuous complex fractionated electrograms (CFE). FIG. 10A shows exemplified bipolar fractionated electrograms including rapid activity and continuous electrograms with high, medium and low similarity indices. The envelop function of the filtered data (dotted line) and start points of the CFE deflections (triangle) are shown. Each LAW consists of multiple deflections and some of those might be CFE deflections. FIG. 10B shows LAWs obtained from the electrograms with high, medium and low similarity indices in FIG. 10A. The normalized electrograms of all the LAWs overlap with their center peaks and corresponding similarity index. Note that in addition to the high morphological similarity of the LAWs in the high similarity site, the CFE deflections (triangle label) are temporally well aligned.

The averaged similarity index of the targeted CFEs was higher in terms of procedural termination and AF recurrence. A disparity of the similarity was not observed in the non-continuous CFEs (0.51±0.09 vs. 0.51±0.11, P=NS) and non-CFEs (0.41±0.13 vs. 0.44±0.11, P=NS, in the patients with and without termination, respectively.

In patients with procedural termination, the termination sites (N=27) were characterized by a significantly higher similarity index compared to the other ablation sites (0.65±0.086 vs. 0.56±0.076, P=0.0001).

Figure 11A:
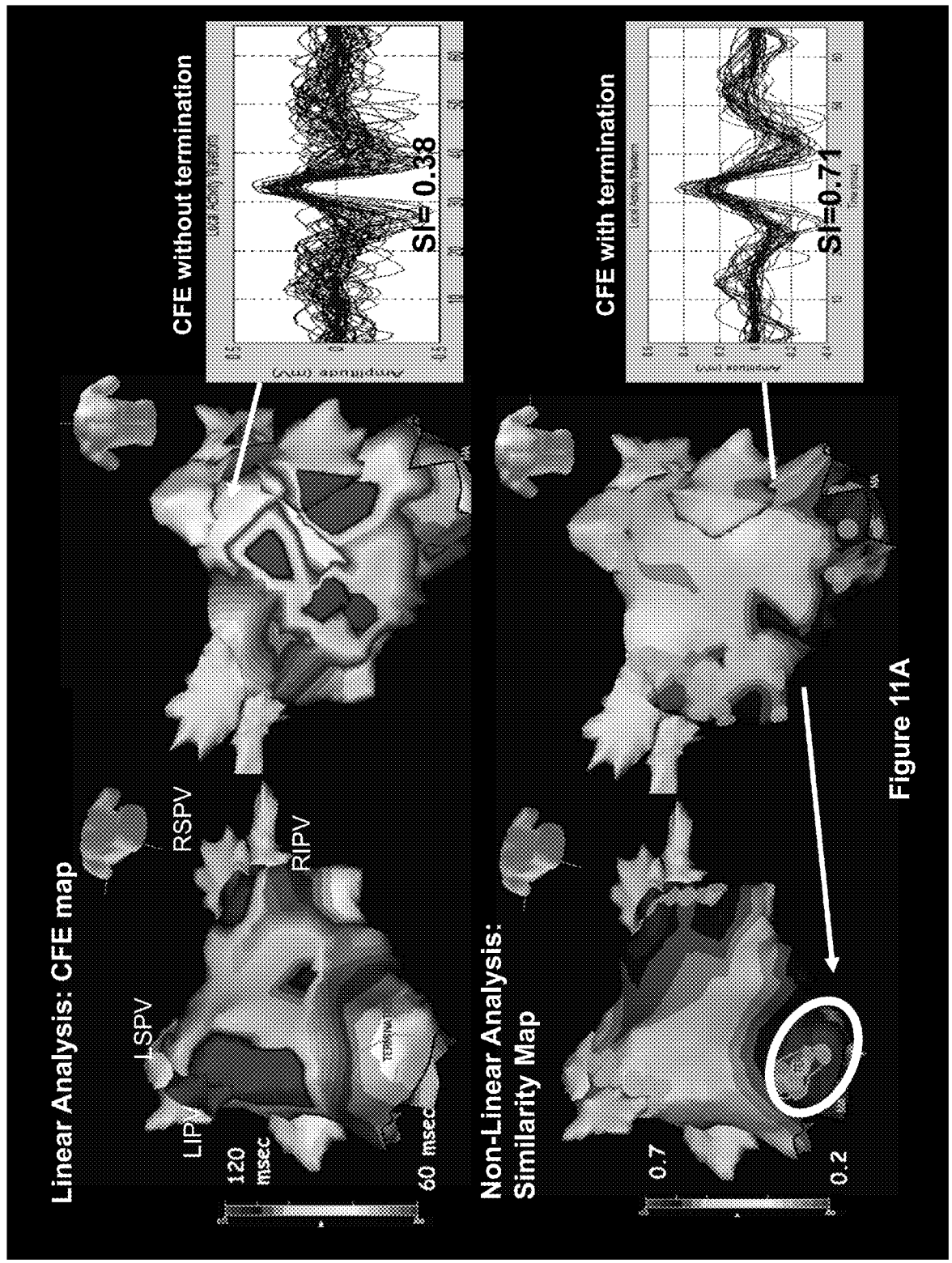
FIG. 11A shows exemplified 3D similarity map and fractionation map in patients with procedural AF termination.
Figure 11B:
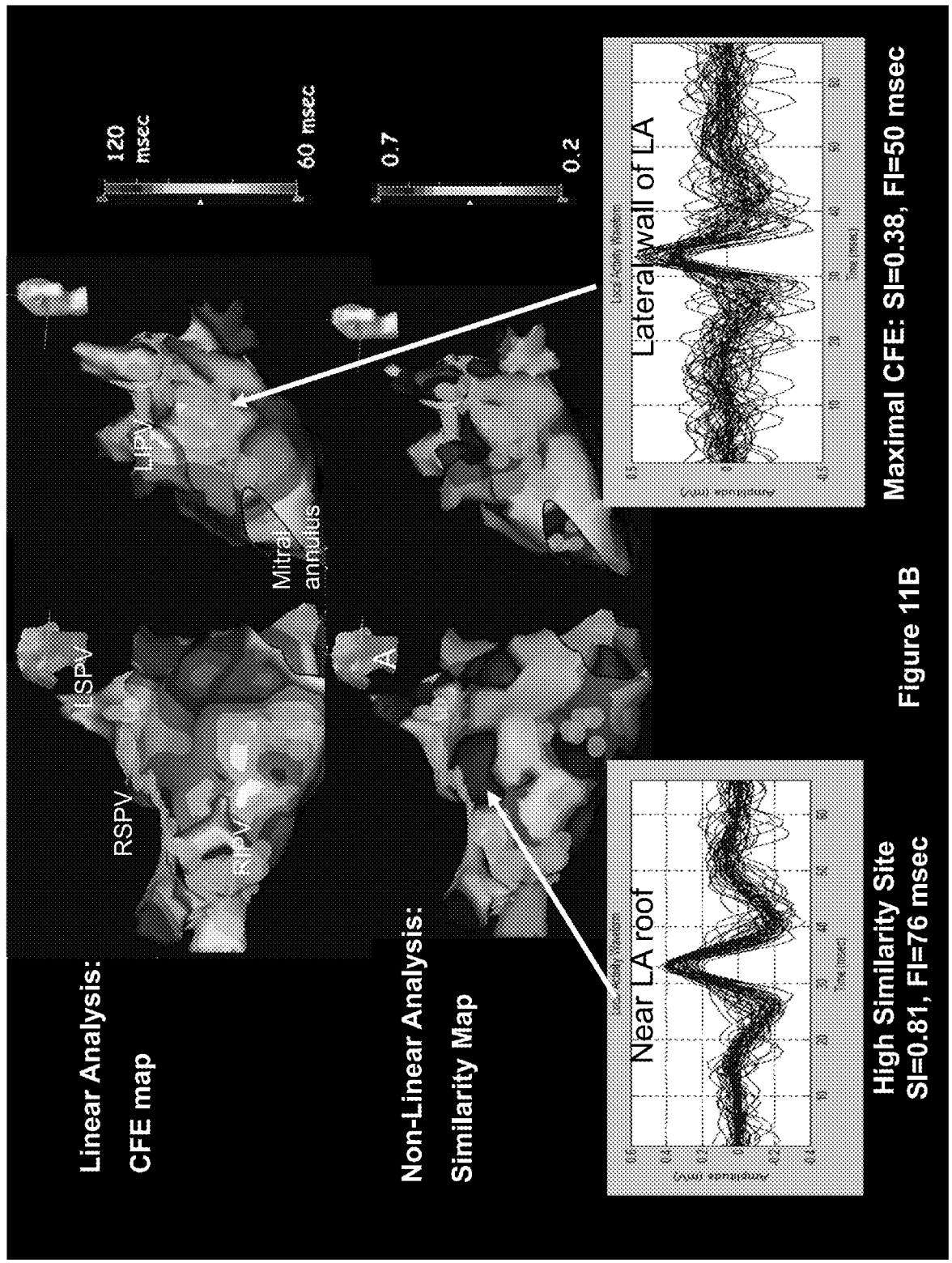
FIG. 11B shows exemplified 3D similarity map and fractionation map in patients without procedural AF termination.

FIGS. 11A and 11B show examples of 3D similarity map and fractionation map in a patient with and a patient without procedural AF termination. FIG. 11A shows an example of procedural AF termination at the posterolateral LA, where the high level of SI was compatible with the maximal CFEs. In contrast, in FIG. 11B, maximal CFE ablation in the lateral mitral annulus and LA septum could not terminate AF. Subsequent roof line ablation (with a mean FI of 76 msec, SI=0.81) terminated AF without AF recurrence during long-term follow-up.

In FIG. 11A, the maximal fractionated sites were identified with the high similarity index in the lateral mitral isthmus region. The similarity index locally was 0.71, whereas the similarity index of the CFEs in the anterior wall was 0.38. In contrast, in FIG. 11B, the maximal CFE ablation in the lateral mitral annulus and LA septum could not terminate AF. The maximal CFE was not associated with the high similarity index. The highest similarity near the border of the continuous CFEs was identified in the roof region. In this patient, ablation in the roof region terminated the AF with final SR maintenance during the long-term follow-up. A subsequent roof line ablation (with a mean fibrillation interval of 76 milliseconds, SI=0.81) terminated AF without any AF recurrence during the long-term follow-up.

The Optimal Detection Algorithm for CFEs

Within all the CFE regions (FI<120 msec), a univariate analysis showed that both a shorter mean FI and higher SI were associated with procedural AF termination. The DF value, HI value, and electrogram voltage did not correlate with the termination (P>0.05). A multivariate regression analysis showed that only a higher SI (≥0.57, Odd ratio=4.9, 95%, the confidence interval CI=1.33-18.0, P=0.017) predicted procedural AF termination. Sites with a shorter mean FI did not predict procedural termination (<70 msec, odd ratio=1.69, 95% CI=0.61-4.67, P=0.31).

We analyzed the predictors of the signal characteristics from the procedural termination sites (N=27), and non-terminating ablation sites in patients with and without procedural AF termination (N=7438). FIG. 12A is a plot of a receiver operating characteristic (ROC) curve showing the optimal thresholds in detecting the termination sites within the continuous CFEs based on the algorithm of dominant frequency (DF) value. The ROC curve analysis shows an optimal cut-off threshold value of the DF>10.2 Hz within the continuous CFEs correlated with the termination with a sensitivity of 0.35 (0.12-0.62) and specificity of 0.93 (5% CI=0.90-0.94).

FIG. 12B is a ROC curve showing the optimal threshold for detecting termination sites within the continuous CFEs based on the algorithm of the similarity index. This ROC curve analysis shows an optimal cut-off threshold value of the SI≥0.565 within the continuous CFEs correlated with the termination with a sensitivity of 0.73 (95% CI=0.45-0.92) and specificity of 0.73 (5% CI=0.72-0.74, area under curve=0.781, P<0.001).

On the contrary, using the higher DF value to predict the termination sites was difficult (Cut-off value=10.2 Hz, sensitivity of 0.33 (0.12-0.62), specificity=0.95-0.96, area under curve=0.64, P=0.0586, as shown in FIG. 11A). Thus the disclosed CFE method is a much better predictor than DF for termination site predictions.

The disclosed system and methods can include one or more of the following advantages: within the continuous CFEs, a conventional linear signal analysis could not differentiate the termination sites from non-termination sites. The sites with a high level of fibrillation electrogram repetitiveness at the CFEs are important for AF maintenance. The presently disclosed analysis rules, including 1) proper segmentation and 2) stationarity evaluation to the consecutive fibrillation electrograms, can serve as an effective tool for distinguishing the culprit CFEs from the bystander CFEs in patients with persistent AF, and further refine the current substrate modification procedure.

Figure 13:
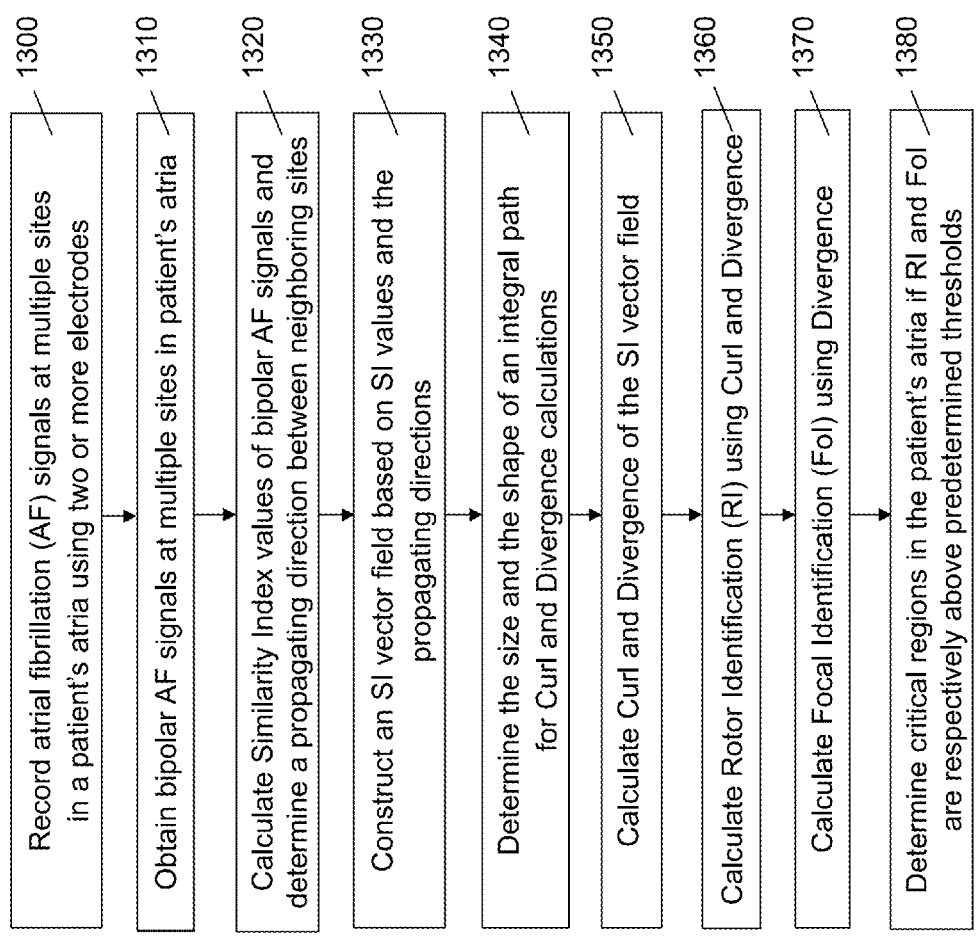
FIG. 13 is a flow diagram for identifying critical rotor regions in patient's atria in accordance to some embodiments of the present invention.
Figure 14A:
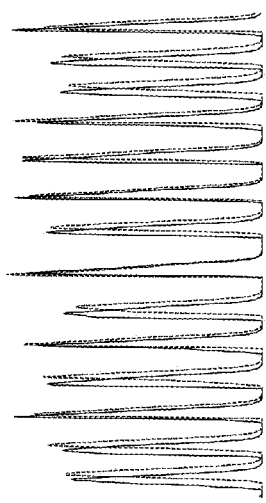
FIG. 14A illustrates exemplified ECG signals (action potential) recorded respectively from an anode and a cathode.

Determining Critical Regions by Identifying Rotors Using Vector Field of Direction Similarity Index In some embodiments, the above disclosed methods shown in FIGS. 2-12B and steps 210-280 shown FIG. 2 and FIG. 8 can be further improved. Similarity index (SI) vectors have been developed based on bipolar AF signals better to predict rotor location in critical regions. Referring to FIGS. 13 and 14A, atrial fibrillation (AF) signals are continuously recorded in time series at multiple sites in a patient's atria using two or more electrodes (step 1300) for 6 seconds. The electrodes include an anode and a cathode. In ECG recording, the AF signals include action potentials, as shown in FIG. 14A, measured respectively at the anode (solid line) and cathode (dashed line).

Figure 14B:
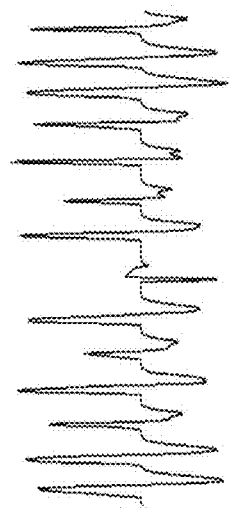
FIG. 14B shows a bipolar AF signal obtained from the ECG signals (action potential) measured from the cathode and the anode.

Bipolar AF signals are then obtained from AF signals measured from the anode and the cathode (step 1310). The bipolar AF signals are obtained at multiple sites in the patient's atria (step 1310). An exemplified bipolar AF signal, as shown in FIG. 14B, is obtained from subtracting the AF signal measured at the cathode (reference electrode) by that obtained from the anode whereas the DC component is removed. The asymmetric shapes of the action potentials, which results in asymmetry between the positive and the negative portions of the bipolar AF signal, reflect systolic time and diastolic time both in atria and ventricle. Similarity index (SI) values can then be calculated based on the bipolar AF signals between neighboring sites (step 1320). A similarity index can first be calculated for each of the positive and negative portions of the bipolar AF signal shown in FIG. 14B, using the method as in FIG. 2 and as described above. The discrepancy between the systole and diastole periods results in different SI values for the positive and the negative portions of the bipolar AF signal, which defines the propagating direction of the AF signal: a larger positive SI represents a forward direction from the anode to the cathode; and a larger negative SI represents a backward direction from cathode to the anode for the negative bipolar signal. The polarity of the bipolar AF signal thus reflects the nature of discrepancy between systole and diastole.

Figure 14C:
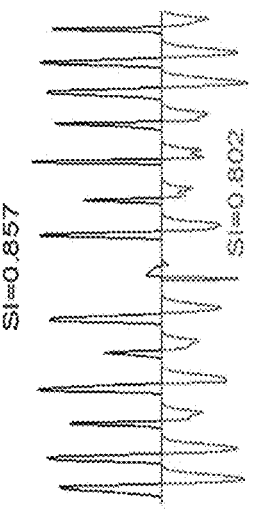
FIG. 14C illustrates similarity indices respectively calculated from the positive portion and the negative portion of the bipolar AF signal.

As shown in FIG. 14C, the similarity index (SI) for the positive portion of the bipolar AF signal is 0.857; and SI is 0.802 for the negative portion of the bipolar AF signal. It is thus determined that the action potential propagates like a wave in the forward direction from the one electrode (i.e. anode) to another (i.e. the cathode) (step 1320). Thus the bipolar AF signal propagates from the first site (i.e. the anode) to one of its neighboring sites (i.e. cathode) if the first similarity index is larger than the second similarity index associated with the first site and the one of its neighboring sites. The bipolar AF signal propagates from one of its neighboring sites (i.e. cathode) to the first site (i.e. the anode) if the second similarity index is larger than the first similarity index associated with the first site and the one of its neighboring sites. The direction of an SI vector is determined by the propagating direction while the magnitude of the SI vector is determined by the larger one of the first similarity index and the second similarity index. A corroborating evidence for this determination is shown in FIG. 14A in that the action potential at the anode (solid line) leads the action potential at the cathode (dashed line) in time.

The insight to the wave-like behavior of the AF signal (i.e. action potential) allows us to extend the concepts of SI to a SI vector, which indicates the wavefront of the action potential. Action potentials can be measured at a matrix of electrodes such that SI values as well as propagating directions can be calculated between pairs of neighboring electrodes. The SI value and its associated propagating direction between each pair of electrode define a component SI vector (step 1330). At each site, the vector sum of the component SI vectors results in a SI vector associated with the site (step 1330). For example, in a two dimensional grid of electrodes over a substrate, an electrode at each site can form electrode pairs with eight of its neighboring electrodes. The SI vector at this site is constructed by calculating the vector sum of all component SI vectors with the eight adjacent sites. A SI vector field can thus be constructed with SI vectors at all measured sites (step 1330).

A SI vector field can be quantized by two physical operators: Curl and Divergence. Curl shows if a vector field is rotational, whereas divergence shows if a vector field spreads out from a source or converges in toward a sink. Curl and Divergence can respectively calculated based on Stokes' theorem and Gauss's theorem.

An aspect of the presently disclosed SI vector field analysis is an integral path along a closed loop when "Curl" and "Divergence" are calculated. The size and the shape of the closed loop are first determined (step 1340). The closed loop can be implemented as a full circle having a radius R. The radius R can be decided adaptively by taking account of the size of the heart, distance of nearest electrodes, and the firing rate. In the disclosed method, the integral path is kept along or within the heart boundary because problems can arise when the integral path is set outside the heart boundary.

To characterize an SI vector field, Curl and Divergence of the SI vector field are calculated (step 1350). In some embodiments, the Curl and Divergence calculations are calculated along an integral path such as a full circle having a radius R.

Curl and Divergence are two differential operators. According to Stoke's theorem, the surface integral of the Curl of a SI vector field over a surface S in real three-space equals to the closed loop integral of the SI vector field over the line boundary of S. Physically, the above integration often refers to a current source of magnetic field in electrostatics. Thus we defined the term "Curl" as the integration in Stoke's theorem per unit length.

$$\int_S (\nabla \times SI) da = \oint SI \cdot dl \quad (4)$$

$$\mathrm{Curl} \equiv \frac{\oint SI \cdot dl}{\oint dl} \quad (5)$$

The Gauss theorem, or divergence theorem, relates the volume integral of the divergence of a SI vector field over a volume V to a surface integral of the field over the boundary of the volume V oriented by outward-pointing normals (S=∂Vn).

$$\int_V (\nabla \cdot SI) d\tau = \oint SI \cdot \hat{n} dS \quad (6)$$

In most cases, the SI vector field can be two dimensional (within the plane of the substrate). Assuming the SI vector field is in a x-y plane in a three dimensional space, the volume integral in equation (6) can be written in cylindrical coordinates $d\tau = rdrd\Theta dz$.

$$\int_V (\nabla \cdot SI) r\, dr\, d\Theta\, dz = \int\int (\nabla \cdot SI) r\, dr\, d\Theta \int dz \quad (7)$$

The surface integral on the right hand side of equation (6) can be written as the addition of two surfaces.

$$\oint SI \cdot \hat{n}\, dS = \int (SI \cdot \hat{r}) r\, d\Theta \int dz + \iint (SI \cdot \hat{z}) r\, dr\, d\Theta \quad (8)$$

Because the SI vector has no component at z direction, the Gauss's theorem on the 2-dimensional vector field was:

$$\iint (\nabla \cdot SI) r\, dr\, d\Theta \int dz = \int (SI \cdot \hat{r}) r\, d\Theta \int dz \quad (9)$$

The term "Divergence" in this paper was defined as the following where $dl = rd\Theta$ $$\text{Divergence} \equiv \frac{\oint (SI \cdot \hat{r}) dl}{\oint dl}. \quad (10)$$

In the disclosed method, the characteristics of patient's atria can be characterized by two parameters based on the Curl and Divergence of the SI vector field: Rotor Identification (RI) and Focal Identification (FoI). RI is defined as the product of Curl and Divergence. RI of the SI vector field is next calculated (step 1360). On the other hand, FoI is defined as the square of Divergence. Focal Identification of the SI vector field is also calculated (step 1370).

RI is mathematically defined as the product of Curl and Divergence.

$$RI \equiv (\text{Div.} > 0) * \text{Div.} * \text{Curl} \quad (11)$$

RI represents wave propagation rotating around a center of a rotor and spreading outward to the periphery of rotor.

On the other hand, FoI is defined as the square of Divergence, which characterizes wave propagation spreading out both around and outside the focal points:

$$FoI = (\text{Div.} > 0) * \text{Div.} * \text{Div.} \quad (12)$$

Thresholds for each of RI and FoI have been derived from simulation observations. A region in atria that has RI above a first such predetermined threshold (e.g. 0.45) and FoI above a second such predetermined threshold (e.g. 0.45), the region can be considered as a source of a rotor point or a focal point, and thus can be treated as a critical region in the patient's atria (step 1380). Using RI and FoI, the disclosed method can effectively identify small-radius reentry rotors in highly fractionated electrograms recorded from patients with persistent AF. The critical regions identified based on the rotor locations are suitable for atrial substrate modification with CFE ablation.

Successful Tracking Meta-Stable Rotors Using the Disclosed Method

A successful application of the disclosed SI vector field based method has been demonstrated by the tracking of metastable rotors, which are very difficult or impossible to be tracked by convention techniques. A cellular automaton model comprising two-dimension excitable media was established to simulate a patient's atrial substrate. Cells on the substrate can be at an excited state or recovery state based on the rules relating to action potentials and neighboured cells. The potentials of all cells were recorded over time and showed changeable wavelike patterns. Then the recording data were transformed to pseudo action potential.

Excitable media are a spatially distributed system that can show signals propagating undamped over long distances. In excitable media, wave propagation can be modelled by continuous partial differential equations (PDEs) and discrete cellular automata. For example, the excitable media could be described by a pair of PDEs for an excitation variable (u) and a recovery variable (v) as follows:

$$\frac{\partial u}{\partial t} = D_1 \nabla^2 u + f(u, v), \quad (13)$$

$$\frac{\partial v}{\partial t} = D_2 \nabla^2 v + \varepsilon g(u, v), \quad (14)$$

wherein $\nabla^2$ is the Laplacian operator, $D_1$ and $D_2$ are diffusion coefficients, and f(u,v), g(u,v) specify the local interaction between u and v. Normally, the depolarization changes on a faster time scale compared to the repolarization in a cycle of action potential, which means that the excitation variable u changes faster than the recovery variable v. So the constant $\epsilon$ in equation (14) should be taken small positive value.

In cellular automaton models of excitation media, the potential of a cell is described by a single variable V that take the integer values 0, 1, 2, ..., N in which zero is the rest state, 0, 1, 2, ..., d ($1 \leq d < N$) are excited states, and d+1, ..., N are refractory states. A cellular automaton is designed to mimic the PDE system while retaining the advantages of the discrete model. The excitation variable u only takes two values: 0 (unexcited) and 1 (exited); meanwhile the recovery variable v is taken as dynamical potential of cell. The increase and decrease of variable v are expressed as $$v_{t+1} = \min\{v_t + g_{up}, V_{max}\}: \text{when } u = 1, \quad (15)$$

$$v_{t+1} = \min\{v_t - g_{down}, 0\}: \text{when } u = 0, \quad (16)$$

where $g_{up}$ and $g_{down}$ are positive integers. When u=1, the recovery variable v increases until $v = V_{max}$. While $v = V_{max}$, u switches to the unexcited state (u=0) and v decreases until v reaches a stable rest state (v=0). In this model, the excitable media is divided into 150×150 cells with different excitability. Each cell can be either in excited or recovering states based on the interactions with its neighbor cells. The electrogram signals are further reconstructed from the dynamical voltages of cells to pseudo action potentials.

Figure 15A:
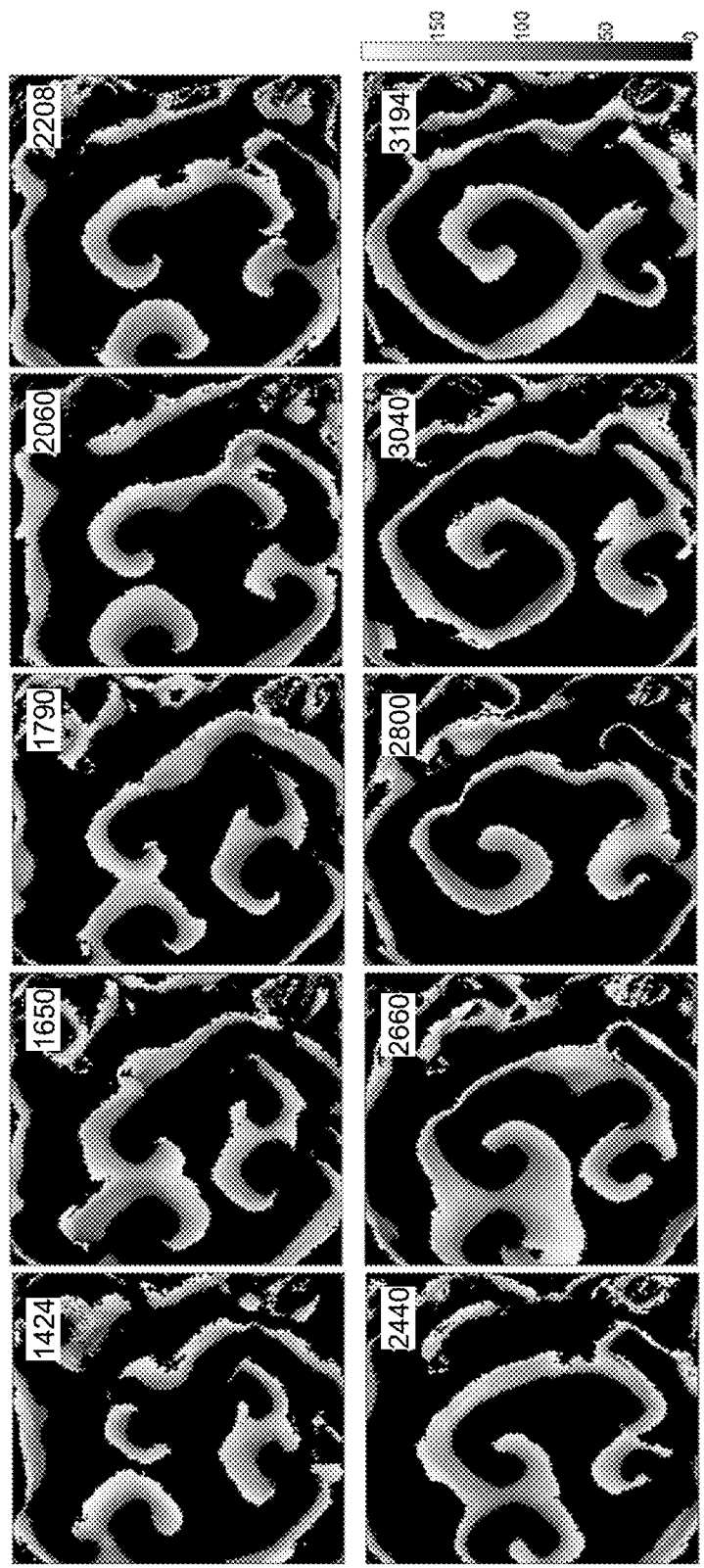
FIG. 15A illustrates the evolution of metastable rotors obtained from a cellular automaton model.

An excitable media with unstable activation wavefront has been demonstrated using the cellular automaton model. Some unstable rotors and wave breaks have been observed to evolve on excitable media. FIG. 15A illustrates an interesting example in which three metastable rotors evolve to become two rotors. The evolution of metastable rotors is captured in ten snapshots of activation wavefront (light color) in simulated times 1400 to 3200. At the middle left of the screen, two metastable rotors stayed with the left one clockwise and the right counterclockwise before simulated time 2660. Another counterclockwise rotor is positioned at the bottom left. After simulated time 2660, wave breaking occurs at the site of the clockwise rotor, and that rotor vanishes at simulated time 2800. From simulated time 2800, the wavefront of another rotor propagates to the left and two metastable rotors remained.

Figure 15B:
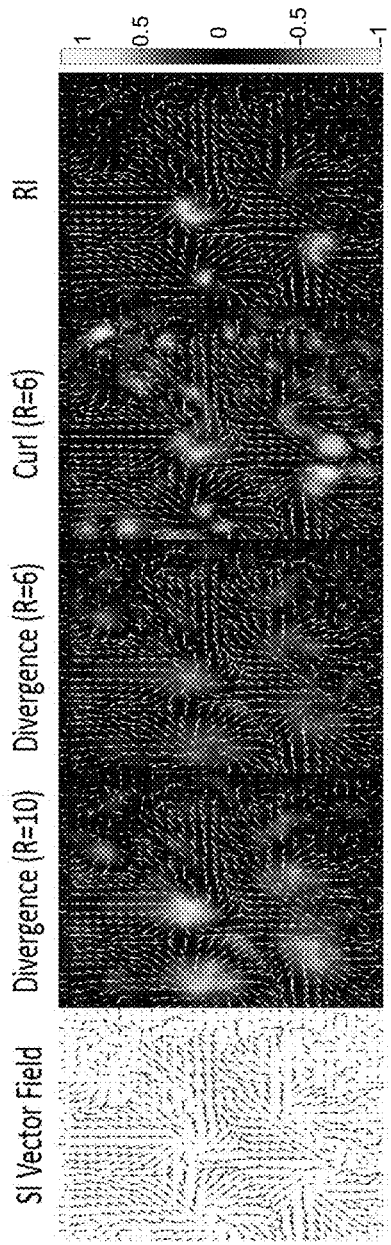
FIG. 15B shows SI vector field, Divergence, Curl, and RI calculated based on SI values obtained within an interval between 1300 and 2300 and in a closed loop having a radius R.

The SI vector fields were calculated within different intervals of time. FIG. 15B respectively shows the SI field, Divergence with a Radius equal to 10, Divergence with a Radius equal to 6, Curl, and RI, which show three rotors.

Figure 15C:
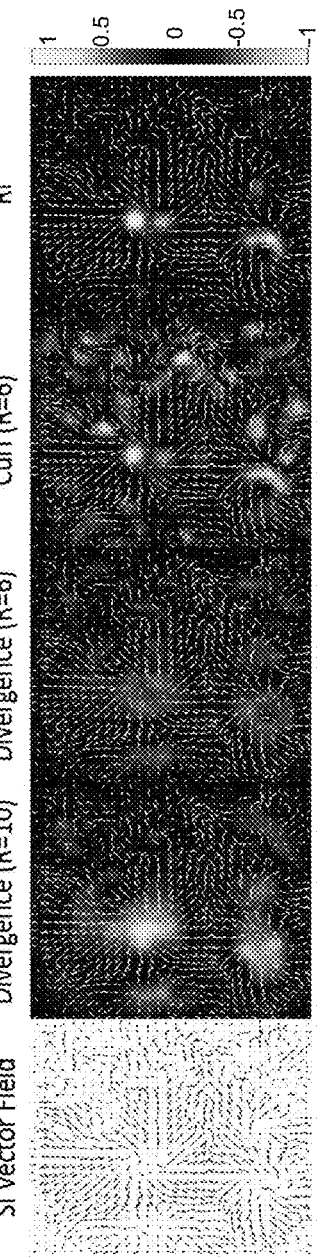
FIG. 15C shows SI vector field, Divergence, Curl, and RI calculated based on SI values obtained within an interval between 2300 and 3300 and in a closed loop having a radius R.
Figure 15D:
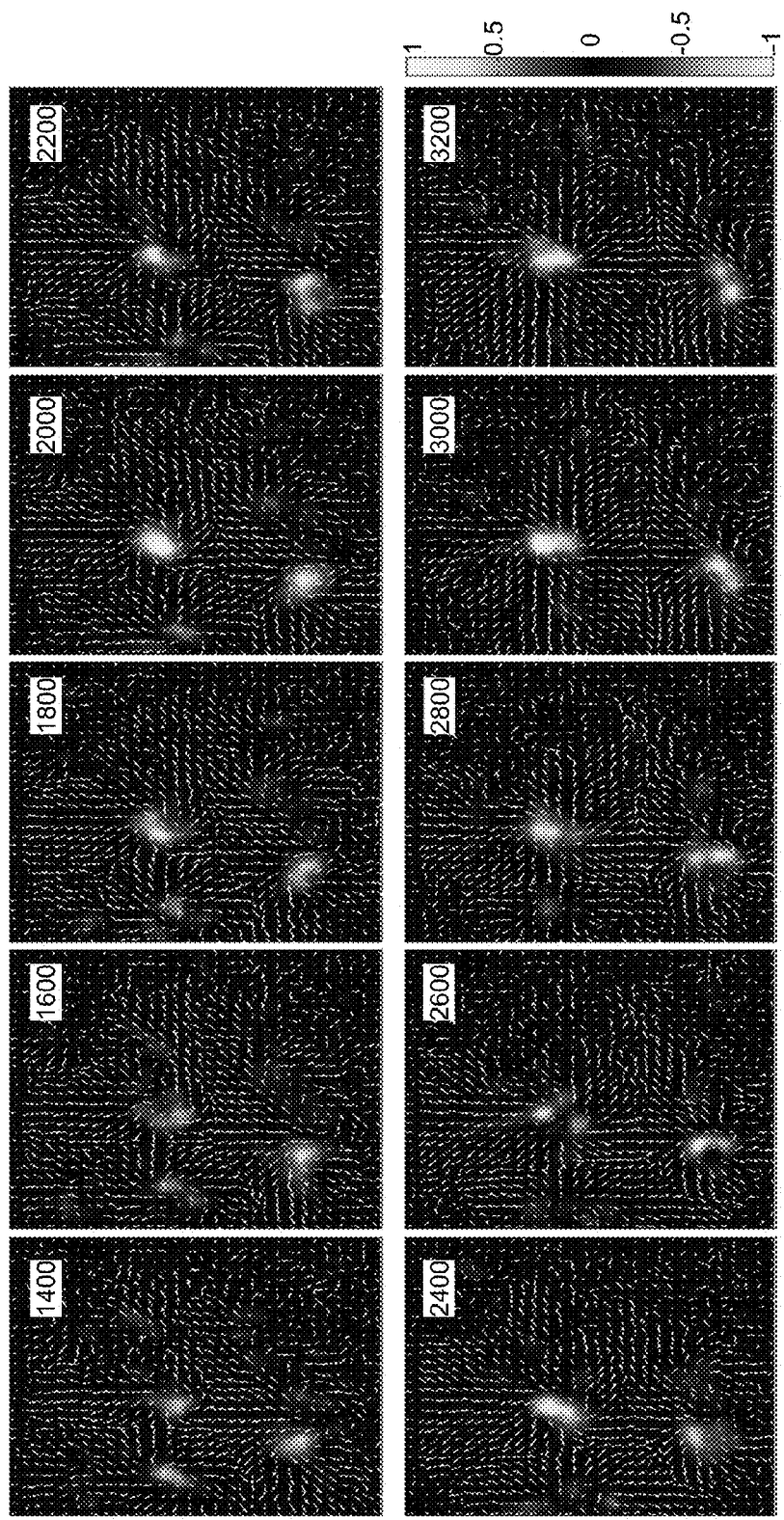
FIG. 15D illustrates ten maps of RI calculated based on SI values obtained within 600 interval of time.

The underlying SI was calculated over a period of simulation times 1300 to 2300. FIG. 15C shows two rotors that forms in simulation times 2300 to 3300. The transitions of metastable rotors are shown a series of RI maps in FIG. 15D. The clockwise rotor (blue color) at the middle left gradually vanished until 2800. Each RI map is calculated from data within an interval of 600 simulation time. For example, the first RI map marked by simulation time 1400 was calculated from the data within the interval of simulation times 1100 and 1700. This example shows that with a proper time interval (e.g. 600), the disclosed method based on SI vector can track the transient dynamic states of rotors even if they are only metastable.

Figure 16A:
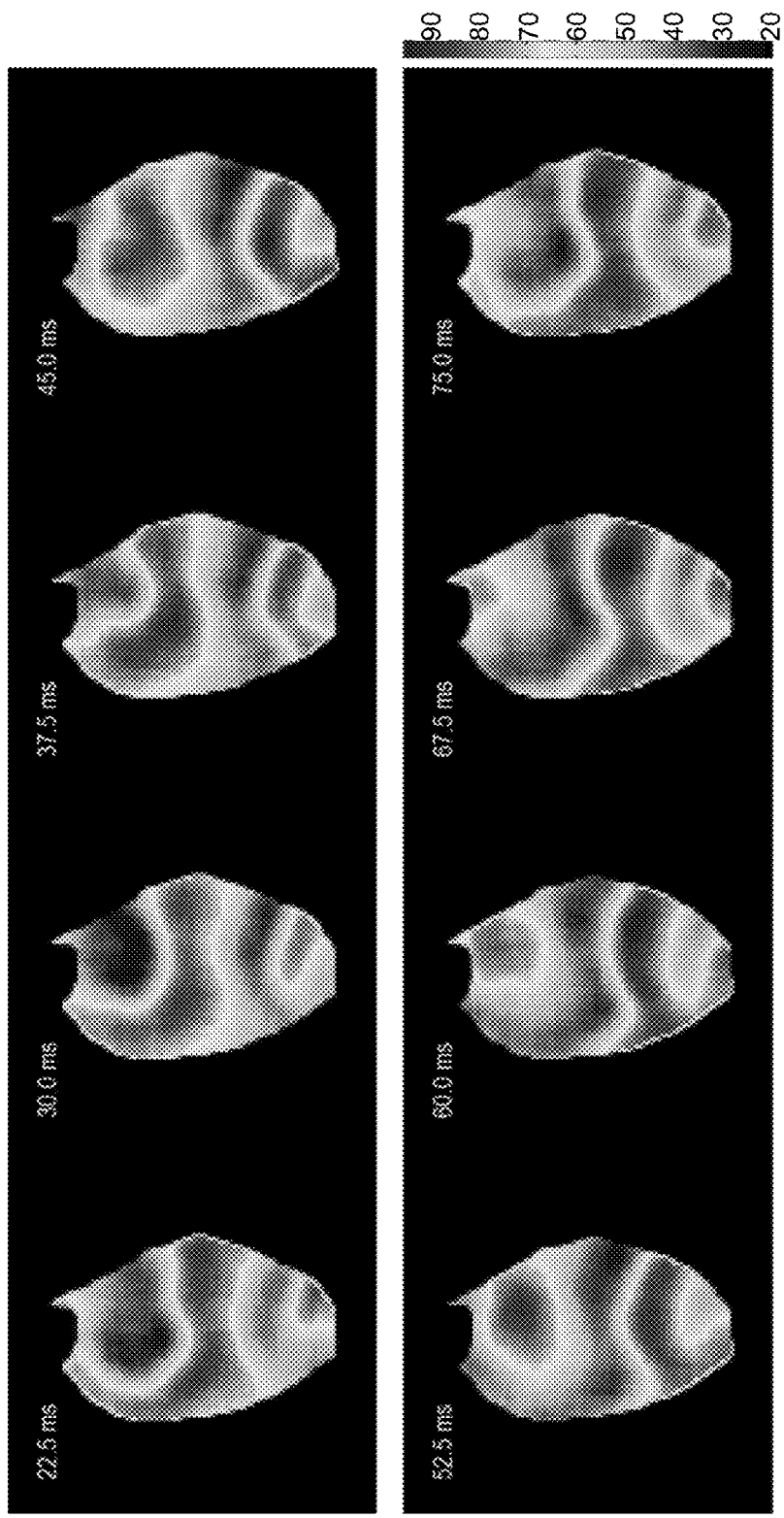
FIGS. 16A-16C illustrate an episode with a counter-clockwise rotor at the bottom of heart.

The presently disclosed methods are demonstrated by defibrillations in ischemic rabbit heart and recording morphological changes of membrane potential of epicardial surface (ventricle) by optical mapping. The recorded data was transferred to pseudo ECG data and the activations were shown in animation. The first example of an episode was shown in FIG. 16A. FIG. 16A shows a series of snapshots of epicardial surface with activations color-coded and the wavefront indicated by red color. A stable rotor circled counter-clockwise around the bottom of heart, which was visible at the anterior surface of heart. Time from 22.5 ms to 45.0 ms, the cells at the bottom right of heart depolarized and this wavefront propagated from the bottom right to bottom left then went down to the bottom. During 52.5 ms to 75.0 ms, the bottom wavefront went back to the bottom right and completed a bcycle of rotational activity. At 67.5 ms, the bottom wavefront separated into two parts in the screen. The upper part of the wavefront gradually moved upward and vanished. Thus a counter-clockwise rotor is determined at the bottom of the wavefront. There was no source elsewhere because the wavefront in the middle and top portions came from below. A source is a location from which a wavefront originates and propagates to elsewhere. The rotational activity at the bottom repeated throughout whole recording time (2250 msec) with an averaged cycle length of 55.56 msec.

Figure 16B:
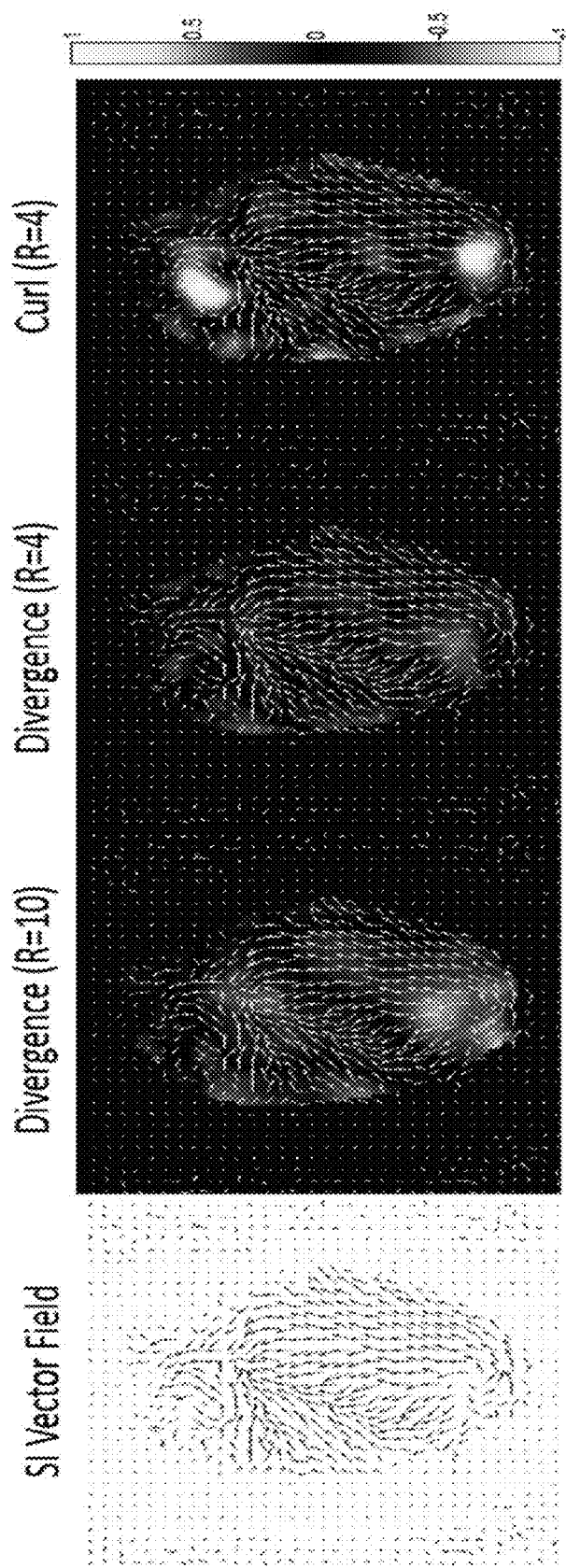
Figure 16C:
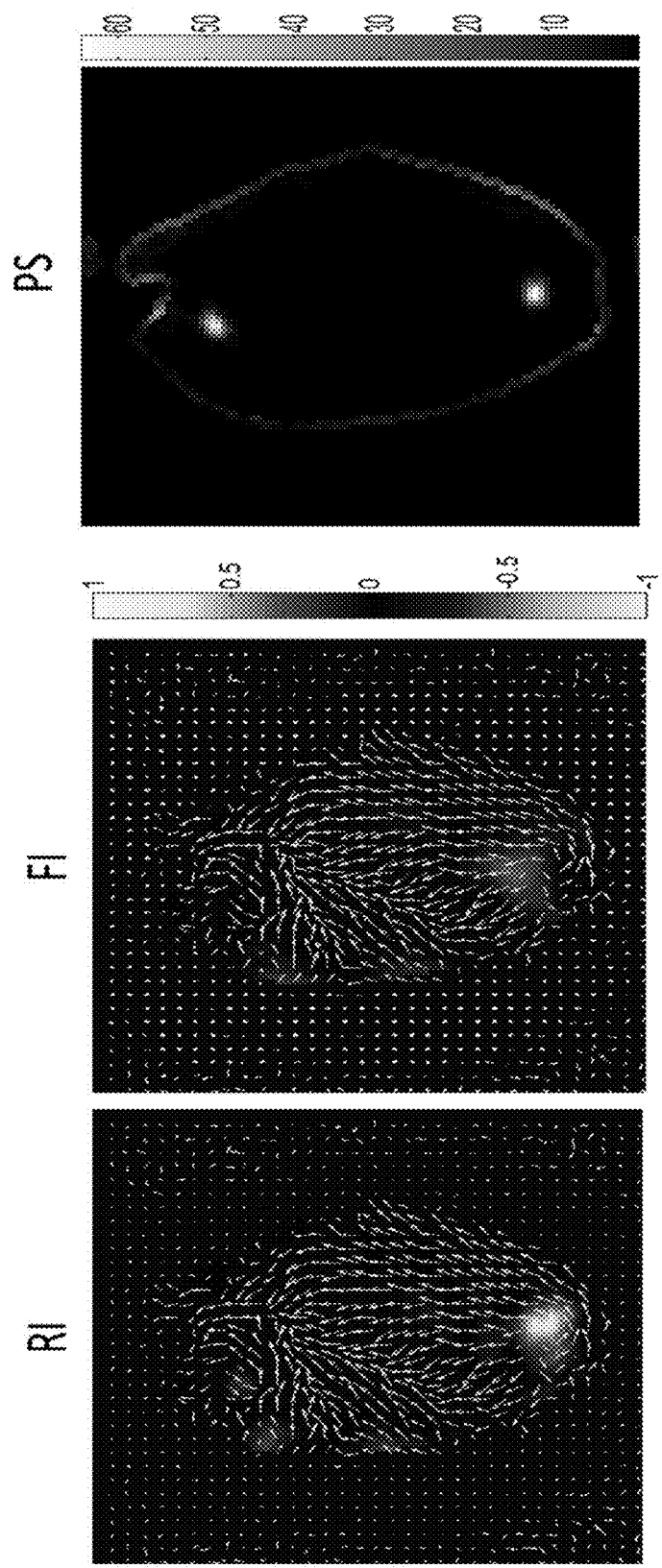

A SI vector field was constructed and the physical operators were calculated and plotted in FIG. 16B, which fit the observations mentioned above. The SI vector field represented the propagation of wavefront. Most of vectors directed upwards and a rotational field was presented at the bottom of heart. A divergence field was calculated from an integration in Equation (12) with R=10 on the 100×100 system. The positive part (red) expressed at the bottom where the flow of vector came from and the negative part (blue) revealed the sink of flows on the top. Another divergence field and curl field were calculated from integration with R=4. There were no obvious small source existing in divergence filed (R=4) but two sites with counter-clockwise rotational fields are observed in the curl field. Finally, maps of RI, FoI, and phase singularity (PS) were shown in FIG. 16C. It was clear that the disclosed method of SI vector field captured no focal source but a counter-clockwise rotor at the bottom of heart. In contrast to method of PS which captured an additional source at the top, the validity of the disclosed method based on SI vector field is confirmed by being in agreement with manual observations.

Figure 17:
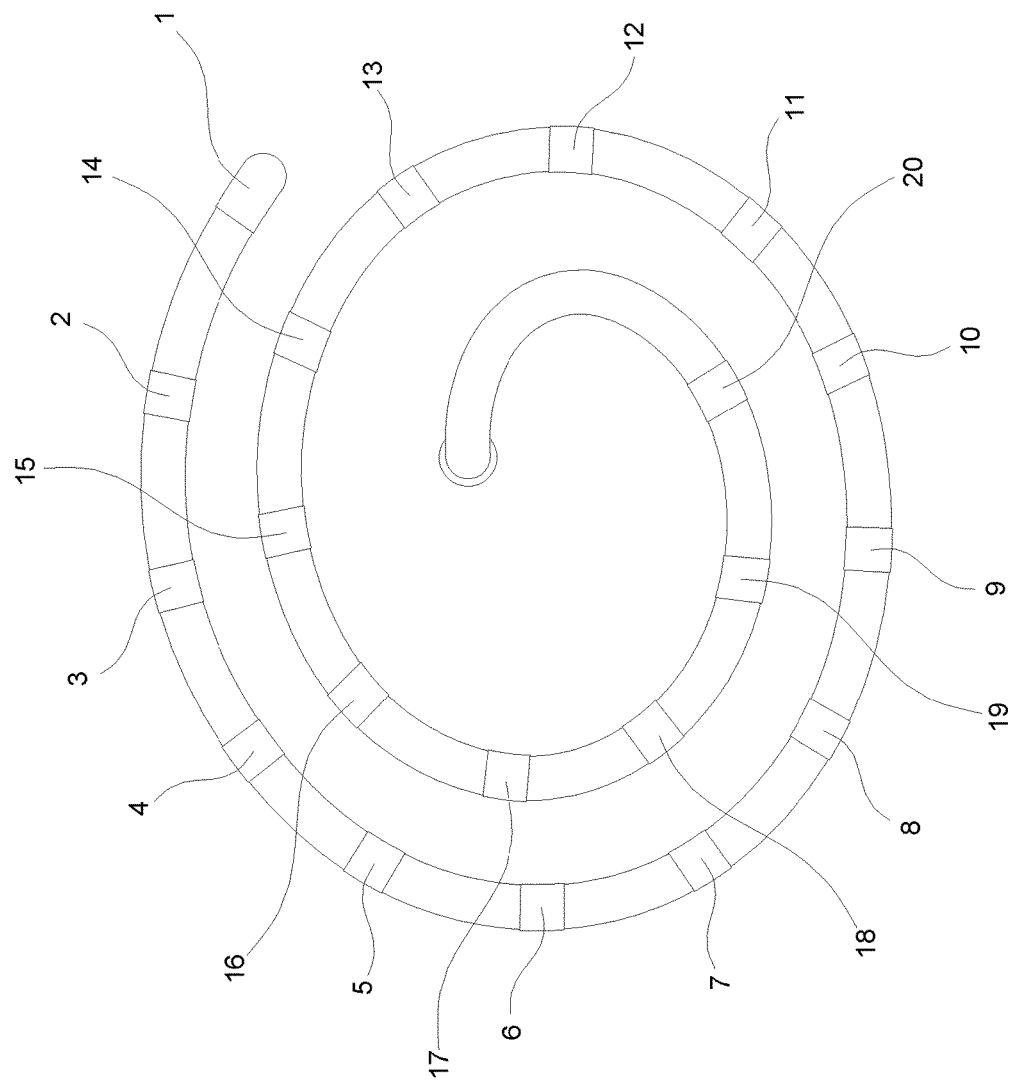
FIG. 17 shows a double spiral medical device comprising twenty electrodes that are compatible with the presently disclosed invention.

The presently disclosed methods are compatible with different configurations of electrodes. For example, a grid of electrodes that are distributed in a matrix of square or hexagonal cells as described above. In another example, as shown in FIG. 17, a double spiral medical device comprising 20 electrodes has been made to investigate simulated rotors for human AF therapies. The 20 electrodes in the double spiral medical device are numbered and mapped to simulated substrates. Using the steps described above, the SI vectors and physical operators were calculated based on the 20 electrodes. For example, to construct a Curl field, the SI vector at electrode 11 was calculated from the bipolar AF signals between electrode 11 and its nearest neighboring electrodes 10, 12 and 20. A simulated substrate was set to be 150×150 grids, or 115×115 $mm^2$. A 23×23 $mm^2$ double spiral attached and moved on the different sites of substrate. Curl filed map was able to demonstrate existence of rotors, as well as rotating and divergent properties around the rotors.

In the present specification, the invention has been described using particular implementation examples. However, it should be obvious that configurations and steps can be varied without departing from the spirit and scope of the present invention. Therefore, the specification and drawings should be considered for illustrative but not restrictive, purpose.

What is claimed is:

1. A computer-assisted method for quantitatively characterizing atrial fibrillation in a patient, comprising:
    recording time series of bipolar atrial fibrillation (AF) signals between a first site and its neighboring sites in a patient's atria using two or more electrodes;
    calculating a similarity index (SI) vector by a computer system based on the bipolar AF signal between the first site and its neighboring sites, comprising the steps of:
        segmenting the time series of the AF signal into activation segments;
        obtaining local activation waveforms (LAW) from the activation segments;
        calculating a distance between a pair of LAWs from the activation segments by computing a scalar product of the pair of LAWs;
        calculating SI based on distances between the LAWs obtained from the activation segments; and
        determining a propagating direction of the bipolar AF signal between pairs of the neighboring two or more electrodes based on a sign of the bipolar AF signal;
    constructing an SI vector field based on SI vectors and the propagating direction of the bipolar AF signal at different sites;
    calculating Curl and Divergence of the SI vector field;
    calculating Rotor Identification (RI) using a product of Curl and Divergence to obtain a map of RI in the patient's atria;
    calculating Focal Identification (FoI) using a square of Divergence to obtain a map of FoI in the patient's atria;
    determining one or more critical regions in the patient's atria by locating local peaks respectively in the map of RI and local peaks in the map of FoI; and
    modifying the one or more critical regions in the patient's atria with complex fractionated electrogram (CFE) ablation.

2. The computer-assisted method of claim 1, wherein the one or more critical regions are determined by tracking movements of local peaks in the map of RI and local peaks in the map of FoI.

3. The computer-assisted method of claim 1, wherein the bipolar AF signals are recorded in time series at multiple sites in a patient's atria, wherein the SI vector field demonstrates wave propagations in the time series.

4. The computer-assisted method of claim 1, further comprising:

selecting a size and a shape of an integral path along or within heart boundary of the patient in the step of calculating Curl and Divergence of the SI vector field.

5. The computer-assisted method of claim 1, wherein the step of calculating SI comprises:
  calculating a first similarity index based on distance between the LAWs obtained from positive portions of the AF signal in the activation segments;
  calculating a second similarity index based on distance between the LAWs obtained from negative portions of the AF signal in the activation segments; and
  determining a propagating direction of the bipolar AF signal by comparing the first similarity index to the second similarity index.

6. The computer-assisted method of claim 5, wherein the propagating direction of the bipolar AF signal is from the first site to one of its neighboring sites if the first similarity index is larger than the second similarity index between the first site and the one of its neighboring sites.

7. The computer-assisted method of claim 5, wherein the propagating direction of the bipolar AF signal is from one of its neighboring sites to the first site if the first similarity index is larger than the second similarity index between the first site and the one of its neighboring sites.

8. The computer-assisted method of claim 5, wherein the SI vector is determined by the propagating direction and a larger one of the first similarity index and the second similarity index.

9. The computer-assisted method of claim 1, wherein the activation segments in the step of calculating a SI vector are sequential in the time series of the AF signal.

10. The computer-assisted method of claim 1, wherein the step of calculating SI based on distances between the LAWs obtained from the activation segments further comprises:
  representing each one of the LAWs by a vector based on strengths of the AF signal at a plurality of sampling points in a respective one of the LAWs; and
  computing a distance between vectors of a pair of LAWs obtained from the same time series of the AF signal to determine degrees of similarity between the pair of LAWs by computing a scalar product of the pair of LAWs.

11. The computer-assisted method of claim 10, wherein the distances are calculated between successive LAWs or between non-adjacent LAWs.

12. The computer-assisted method of claim 1, wherein the activation segments are identified at least in part based on overlapping of local maxima in the time series of the AF signal.

13. The computer-assisted method of claim 1, wherein the step of calculating SI based on distances between the LAWs obtained from the activation segments further comprises:
  normalizing the LAWs in the activation segments before the step of determining degrees of similarity between LAWs.

* * * * *